(12) United States Patent
Taidi et al.

(10) Patent No.: US 9,193,944 B2
(45) Date of Patent: Nov. 24, 2015

(54) METHOD FOR OBTAINING CONCENTRATED POLYPHENOL EXTRACTS FROM A STIRRING PROCESS

(75) Inventors: Behnam Taidi, Strasbourg (FR); Jean-François Doriat, Velaine-en-Haye (FR); Jean-Yves Malpote, Griesheim sur Souffel (FR)

(73) Assignee: Brasseries Kronenbourg, Strasbourg (FR)

( * ) Notice: Subject to any disclaimer, the term of this patent is extended or adjusted under 35 U.S.C. 154(b) by 192 days.

(21) Appl. No.: 12/937,122

(22) PCT Filed: Apr. 10, 2009

(86) PCT No.: PCT/FR2009/000417
§ 371 (c)(1),
(2), (4) Date: Dec. 9, 2010

(87) PCT Pub. No.: WO2009/144406
PCT Pub. Date: Dec. 3, 2009

(65) Prior Publication Data
US 2011/0091582 A1    Apr. 21, 2011

(30) Foreign Application Priority Data
Apr. 11, 2008 (EP) .................................... 08290357

(51) Int. Cl.
| A61K 36/00 | (2006.01) |
| A61K 36/899 | (2006.01) |
| C12F 3/06 | (2006.01) |
| A23L 1/30 | (2006.01) |
| A61K 8/97 | (2006.01) |
| A61Q 19/08 | (2006.01) |
| C12H 1/056 | (2006.01) |

(52) U.S. Cl.
CPC ................. *C12F 3/06* (2013.01); *A23L 1/3002* (2013.01); *A61K 8/97* (2013.01); *A61Q 19/08* (2013.01); *C12H 1/0424* (2013.01); *A23V 2002/00* (2013.01); *A61K 2800/522* (2013.01); *A61K 2800/85* (2013.01)

(58) Field of Classification Search
None
See application file for complete search history.

(56) References Cited

U.S. PATENT DOCUMENTS

| 4,910,182 A | 3/1990 | Hums et al. | |
| 2003/0138546 A1* | 7/2003 | Goldstein et al. | 426/600 |
| 2005/0191268 A1 | 9/2005 | Henry et al. | |
| 2007/0254063 A1* | 11/2007 | Aerts et al. | 426/11 |

FOREIGN PATENT DOCUMENTS

| DE | 10 2007 001 349 A1 | 5/2008 |
| JP | 2007039397 | 2/2007 |

OTHER PUBLICATIONS

Gerhauser, et al. (2002) Phytochemistry Reviews, vol. 1, No. 3 pp. 369-377.*
Spencer, J.P.E. (2008) Proc. Nutr. Soc. 67, 238-252.*
Nichols et al. (2010) Arch. Dermatol. Res. 302:71-83.*
Gerhauser, et al. (2002) Phytochemistry Reviews, 1: 369-377.*
McLaughlin et al. (2008) J. Am. Soc. Brew. Chem. 66(3): 174-183.*
Ajila et al. Critical Reviews in Biotechnology, 2010 1-22, Early Online. Printed publication: Sep. 2011: 31(3): 227-49.*
Katiyar et al. (2001) Carcinogenesis vol. 22. No. 2 pp. 287-294.*
Whittle et al. (1999) Journal of the Institute of Brewing vol. 105 No. 2, pp. 89-99.*
Mikyska et al. (2002) J. Inst. Brew. 108(1): 78-85.*
Tedesco et al. (2005) Nutrition and Cancer, 52(1), 74-83.*
Callemien et al. (2008) Food Chemistry 110; 1012-1018.*
Gasowski et al. (2004) J. Nutritional Biochem. 15: 527-533.*
Gorinstein et al. (2007) Inter. J. Food Sci and Nutr. 58(2): 94-107.*
Kirby et al. (1980) J. Inst. Brew. vol. 86, 15-17.*
Raskin et al. (2004) Current Pharma. Design 10, 3419-3429.*
Revilla et al. (1998) J. Agric. Food Chem. 46, 4592-4597.*
Ting et al. (2008) J. Am. Soc. Brew. Chem. 66(2); 116-126.*
Callemien et al., "Use of thiolysis hyphenated to RP-HPLC-ESI(−)-MS/MS for the analysis of flavanoids in fresh lager beers", Food Chemistry, 110:1012-1018 (2008).
Gasowski et al., "The influence of beer with different antioxidant potential on plasma lipids, plasma antioxidant capacity, and bile excretion of rats fed cholesterol-containing and cholesterol-free diets", Journal of Nutritional Biochemistry, 15:527-533 (2004).
Skovenborg, "Red Wine Polyphenols in cancer research", (Nov. 13, 2007) (XP002495489).
Tedesco et al., "Antioxidant and Cytotoxic Properties of Lyophilized Beer Extracts on HL-60 Cell Line", Nutrition and Cancer, 52(1):74-83 (2005).
International Search Report and Written Opinion in corresponding PCT/FR2009/000417 dated Jun. 20, 2011.

* cited by examiner

*Primary Examiner* — Chris R Tate
*Assistant Examiner* — Russell Fiebig
(74) *Attorney, Agent, or Firm* — Morgan, Lewis & Bockius LLP

(57) ABSTRACT

The present invention proposes methods for obtaining concentrated polyphenol extracts resulting from the stirring process, through a step in which a partially purified beer is placed into contact with a resin that adsorbs the polyphenols, followed by a step in which the polyphenols adsorbed onto said resin are recovered. The invention also relates to the extracts thus obtained, which feature remarkable properties, as well as to several applications for these extracts.

4 Claims, 12 Drawing Sheets

Wilcoxon test: $^T p < 0.10$

METHOD FOR OBTAINING CONCENTRATED POLYPHENOL EXTRACTS FROM A STIRRING PROCESS

RELATED APPLICATIONS

Figure 1:
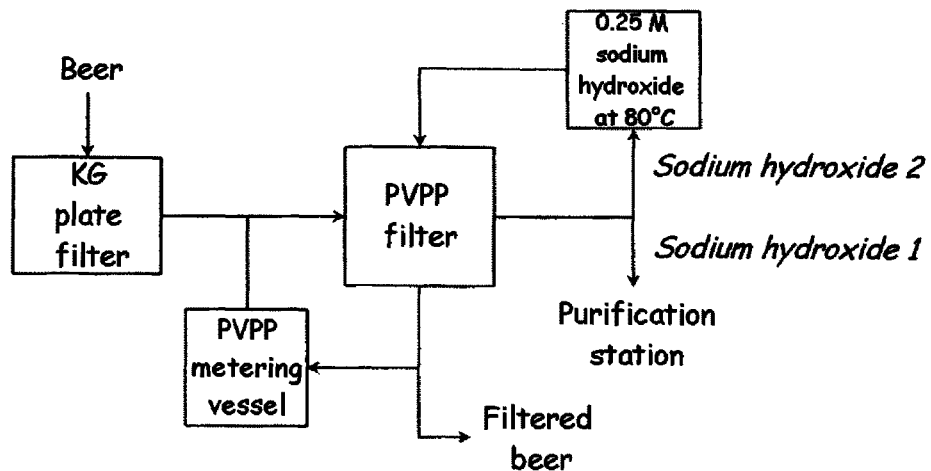

The present application is a U.S. National Phase Application of International Application No. PCT/FR2009/000417 (filed Apr. 10, 2009) which claims priority to European Patent Application No. 08290357.6 (filed Apr. 11, 2008) which are hereby incorporated by reference in their entirety.

The present invention relates to the field of developing the co-products of the brewing industry. In particular, the invention proposes methods for obtaining concentrated polyphenol extracts resulting from the brewing process, and also several applications for these extracts, which display notable properties.

Beer is produced from cereals (essentially barley, to which other cereals, such as wheat, rice or corn can be added), which undergo various treatments. Beer production essentially comprises the following steps:

Malting:

This step serves to activate enzymes in the barley, which convert the starch to sugars during the brewing. The barley, which is a hard cereal rich in insoluble starch, is converted to malt, which is friable and rich in soluble compounds, through the succession of the following three steps: steeping, during which the grain soaks up water, germination, and kiln drying, which stops the germination.

Brewing:

The crushed malt is mixed with 2 to 3 times its volume of water in tanks called "mash tubs"; this operation is called "mashing". After cooking at various temperature stages for 2 to 6 hours, the malt becomes wort. During this operation, the starch contained in the malt is converted to sugar.

The same operation can be carried out in parallel in another tank if a non-malted cereal (raw grain) is used.

The whole is then mixed so as to constitute the mash. Having been filtered a first time and having had the grain husks removed in the filter tank, the mash becomes "liquor". The whole is then transferred into the hop boiler where the wort is cooked at 100° C. for 1 to 2 hours and hops are added in a proportion of 1 to 2 g per liter. The hops give the beer bitterness and flavors and facilitates its storage by virtue of its antiseptic properties.

By extension, the term "brewing" often denotes the entire beer production process (including fermentation).

Fermentation:

Cooled in an exchanger at the desired fermentation temperature, the wort is inoculated with the yeast which will convert the sugar to alcohol, flavors and carbon dioxide. The fermentation lasts a few weeks and is carried out in large fermentation tanks.

Depending on the type of beer desired, the yeasts used are different; for ale-type beers, top fermentation yeasts of *Saccharomyces cerevisisae* type are used, whereas for lager-type beers, bottom fermentation strains of *Saccharomyces uvarum* type are used.

Aging:

The mixture is then filtered so as to give the "green beer" which is placed in aging tanks at a temperature of 0° C. It matures therein for several weeks so as to give rise to the stock ale. During this phase, the beer slowly refines and acquires its bouquet and its taste following the work of the yeast and the cold (N.B.: this second fermentation is not systematically carried out in modern brewing).

Filtration:

The filtration aims to improve the clarity and the brilliance of the beer by removing the last yeasts and the colloidal particles still in suspension. The beer is filtered through kieselguhr filters, kieselguhr being a mineral powder made up of fossilized diatomes (marine microorganisms).

This filtration step is not sufficient. This is because, even after this filtration, the beer can become cloudy in the cold and this cloudiness can become permanent with storage of the beer. This cloudiness is formed by the association of polyphenols with proteins, which results in the formation of insoluble compounds. In order to bypass this problem, the undesirable polyphenols can be removed from the beer by passing it over a resin: PVPP (polyvinyl polypyrrolidone). PVPP is a randomly crosslinked poly[1-(2-oxo-1-pyrrolidinyl)ethylene]. It is produced by polymerization of N-vinyl-2-pyrrolidone in the presence of a caustic catalyst or of an N,N'-divinylimidazolidone. Its chemical formula is $(C_6H_9NO)_n$. At the current time, it is regenerated by washing with sodium hydroxide, and the effluents go down the drain.

Polyphenols (or phenolic compounds) are molecules specific to the plant kingdom. The basic structural element is a benzene ring to which are directly bonded one or more free hydroxyl groups or hydroxyl groups involved in another chemical functional group. More than 8000 compounds correspond to this definition. They are divided up into various families according to their characteristics: phenolic acids, flavonoids, tannins and lignans, which, with isoflavones, are called phytoestrogens. These compounds are used in industry, in particular for their coloring and antioxidant properties.

In this context, the inventors have studied the possibility of recovering the polyphenols removed from the beer at the end of the production thereof. Owing to their general biological properties (antioxidant, biocidal, anti-inflammatory, etc., properties), polyphenols are in fact capable of being of interest in various fields:

cosmetics
food-processing/nutraceutical field
phytotherapy
veterinary medicine
pharmacy.

The polyphenol extracts currently available on the market are derived from the following plant compounds: olives, coffee, cocoa, tea, grape, wine, apple, soya, alga, blackcurrant or pine bark.

Inventors have also studied the advantage of the polyphenols extracted from the beer production process, after the fermentation step, in various applications. Specifically, the phenolic compounds have been subjected to the impact of malting, brewing and fermentation, which has probably led to modifications in their structure (binding to proteins, to polysaccharides, partial oxidation and polymerization). There is a risk of these modifications influencing their properties, in particular their antioxidant properties. Surprisingly, the inventors have demonstrated that the polyphenols resulting from the brewing process (taken in the broad sense) display excellent antioxidant properties.

The present invention therefore relates, firstly, to the use of a partially purified beer as starting material for obtaining a polyphenol-rich extract. The term "partially purified beer" is here intended to mean the beer obtained after removal of the yeast, plant debris and colloidal particles, for example by filtration through kieselguhr filters (other methods, in particular based on centrifugation, have also been described for this purpose). A "polyphenol-rich extract" or "polyphenol extract" or "polyphenol concentrate" here denotes a plant extract in any form (liquid or solid), the total polyphenol content of which is at least 5%, preferably at least 10% for the liquid form, and at least 50%, preferably at least 60% to 80%, or even more, for the solid form. The Folin-Ciocalteu method (EBC standard) can, for example, be used to determine the polyphenol content in the concentrates according to the invention (Folin and Ciocalteu, 1927).

A method for obtaining an extract of polyphenols resulting from the brewing process, comprising at least one step of bringing a partially purified beer into contact with a resin that adsorbs the polyphenols, followed by a step of recovering the polyphenols adsorbed onto said resin, is also part of the present invention. Of course, the expression "brewing process" should here be understood in its broad sense, denoting the beer production process. An example of a resin that can be used to implement this method is PVPP.

The step of "recovering" the polyphenols adsorbed onto the resin after its contact with the partially purified beer involves these polyphenols being desorbed from said resin, placed under conditions guaranteeing their stability and, where appropriate, concentrated and/or purified. This step can, for example, be carried out by using a second resin in order to recover the polyphenols after desorption thereof from the first resin. In one preferred embodiment of the invention, this second resin is hydrophobic and nonionic, and allows desorption of the polyphenols through the use of an organic solvent.

According to one preferred implementation of the invention, the following steps are carried out:
(i) the partially filtered beer is brought into contact with a polyvinylpolypyrrolidone (PVPP) resin;
(ii) the PVPP is washed with an alkaline solution;
(iii) the PVPP washing solution is brought into contact with a second resin that adsorbs the polyphenols;
(iv) the polyphenols are desorbed from the second resin;
(v) the polyphenols are concentrated.

Some preferred implementations of these various steps are detailed below. These particular implementations can be used independently or in combination, in continuous or batch methods.

In step (ii), the PVPP can undergo two washes with sodium hydroxide; in this case, only the sodium hydroxide solution from the first wash or, where appropriate a fraction of this solution, is used in step (iii). Preferably, the sodium hydroxide concentration is between 1% and 2%; even more preferably it is approximately 1.6%. Of course, another alkaline solution can be used in place of the sodium hydroxide.

After desorption of the polyphenols with the alkaline solution, this solution will preferably be rapidly neutralized, or even acidified, in order to prevent degradation of the polyphenols. This is particularly advantageous in the case of a batch method. This is because, in the case of a continuous method, the time during which the polyphenols remain in the alkaline solution can be reduced, so as to do away with the problem of degradation of the polyphenols in an alkaline medium and therefore, optionally, to do away with the neutralization or acidification step. As is described in the experimental section below, phosphoric acid is particularly suitable for neutralizing or acidifying the alkaline solution at the end of step (ii).

The second resin, used in step (iii), will advantageously be a hydrophobic and nonionic, adsorbent polymeric resin which is preferably aromatic. By way of nonlimiting examples of such resins, mention may be made of the Amberlite™ XAD 1180 resin from the company Rohm & Haas S.A.S., and also the food version thereof (Amberlite™ FPX 68), which is a macrocrosslinked adsorbent resin designed for the beverage industry, especially for extracting flavonoids. Amberlite™ FPX 66 resin, which makes it possible to recover smaller molecules compared with FPX 68, can also be used.

A step of rinsing the second resin, with an aqueous solution, will preferably be added between steps (iii) and (iv).

Preferably, the desorption in step (iv) is carried out by passing a solution of alcohol or another organic solvent over the resin. The polyphenols can then be concentrated, for example, by evaporating off the organic solvent. The concentrated solution can be freeze-dried or dried, so as to obtain a powder and to improve the stability of the polyphenol concentrate.

Currently, PVPP is the only resin capable of adsorbing polyphenols and entered on the list of technological auxiliaries authorized in the processing of beer in Europe. However, this list is liable to be modified. A variant of the methods described above is therefore envisioned in accordance with the invention, in which the partially filtered beer is brought into contact directly with a resin that adsorbs the polyphenols and allows their desorption with an organic solvent. For this, a hydrophobic and nonionic adsorbent resin, which is preferably aromatic, such as the XAD 1180, FPX 68 and FPX 66 resins mentioned above, can advantageously be used. This variant makes it possible to be free of the steps of regenerating the sodium hydroxide and neutralizing the acid, reduces the amount of salts and makes it possible to improve the extraction yield and the purity of the polyphenols.

Another aspect of the present invention is a polyphenol concentrate which can be obtained by means of a method as described above. The various steps of the brewing process undergone by these polyphenols give them original properties and in particular a composition rich in catechins and epicatechins, and polymers thereof. A concentrate according to the invention can be in solid form, for example in the form of a powder, or in liquid form, for example in an aqueous or alcoholic solution or in glycerol.

A polyphenol concentrate according to the invention can be used for the preparation of an antioxidant composition, whatever the purpose of this composition.

In particular, the antioxidant properties of the concentrates of the invention makes them excellent candidates as components of cosmetic products. These concentrates can in fact be added to a large diversity of cosmetic products, such as skin moisturizing creams or lotions, solutions for washing or rinsing the skin or the hair, masks, makeup products, etc. The concentrates of the invention can be integrated into cosmetic products as active products, for example, for the antioxidant, moisturizing and stimulating properties thereof, but also as agents for facilitating the storage of the cosmetic products. A cosmetic product according to the invention can, of course, be formulated for topical application, but it can also be formulated for oral application, in the form of gel capsules, lozenges, a syrup, or any other form. The inventors have in fact demonstrated, on a model of skin in culture, a beneficial effect of the polyphenols in contact with epidermal cells, on the quality of the skin. The cosmetic products of the invention can in particular be used for moisturizing the skin and/or preventing or slowing down aging thereof. By way of indication, cosmetic compositions comprising between 0.25% and 0.5% of polyphenol-rich solid extract (comprising approximately 80% of polyphenols) can be advantageously used in these indications.

According to another particular aspect of the invention, the polyphenols resulting from the brewing process are used in a neutraceutical composition such as a functional food or a food supplement. The term "functional food" is intended to mean a food preparation to be consumed as a normal food although it provides benefits that are superior to conventional nutrition. A functional food comprising polyphenols which can be obtained according to the invention is therefore an integral part of the present invention. By way of nonlimiting examples of functional foods according to the invention, mention may be made of fruit juices, sodas and other alcohol-free beverages, cereal-based products, yoghurts and milk preparations, chocolate bars, margarine and other spreadable fats, biscuits, etc.

In addition to their beneficial properties on health, the polyphenols of the invention can be used in foods as preservatives, for example for replacing certain synthetic products such as vitamin C, BHA (butylhydroxyanisole) and BHT (butylhydroxytoluene).

Food supplements comprising a polyphenol concentrate obtained according to the invention are also part of the present invention. These supplements can be, for example, in the form of gel capsules, powders or tablets. Of course, they can contain other active ingredients, such as antioxidant vitamins (in particular C and E), B group vitamins, vitamin D, calcium, magnesium, omega-3 fatty acids, phospholipids, plant extracts, etc.

A particular use of the polyphenol concentrates of the invention, illustrated in the experimental examples hereinafter, is the preparation of a composition intended for improving the cognitive performance levels of an individual. The term "cognitive performance levels" here denotes, in the broad sense, memory, ability to learn, reasoning, but also the ability to concentrate, attention, resistance to stress, reaction speed, etc. Such a composition may be in the form of a food supplement, but also in any other form, in particular galenical form.

According to another aspect, the present invention relates to the use of a polyphenol concentrate which can be obtained by means of a method described above, for the preparation of an anti-aging composition. In particular, such a composition can be used to limit or delay the consequences of aging of the brain, such as memory loss, dementia, etc. Such an anti-aging composition can be intended for human or veterinary use. All the administration forms described above can be envisioned for such a composition.

By way of indication, the polyphenols of the invention can be administered in a proportion of from 100 to 400 mg per day for an adult human.

In addition to the above arrangements, the invention also comprises other arrangements which will emerge from the experimental examples below and from the attached figures.

FIGURE LEGEND

FIG. 1: Scheme of the principle of the PVPP filtration/regeneration.

Figure 2:
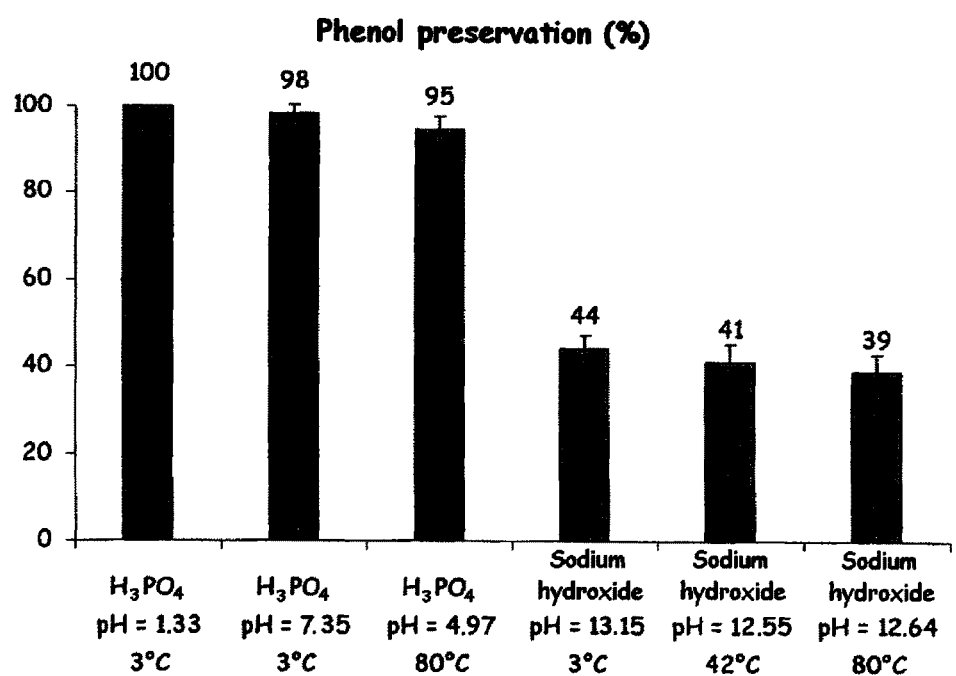

FIG. 2: Polyphenols present in the regeneration solution as a function of the pH.

Figure 3:
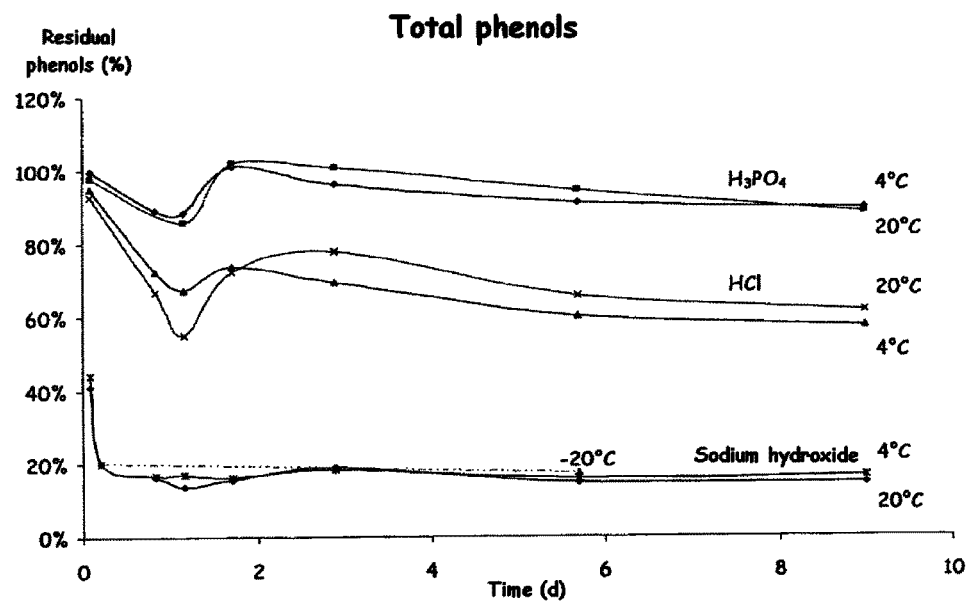

FIG. 3: Change in total polyphenols over time.

Figure 4:
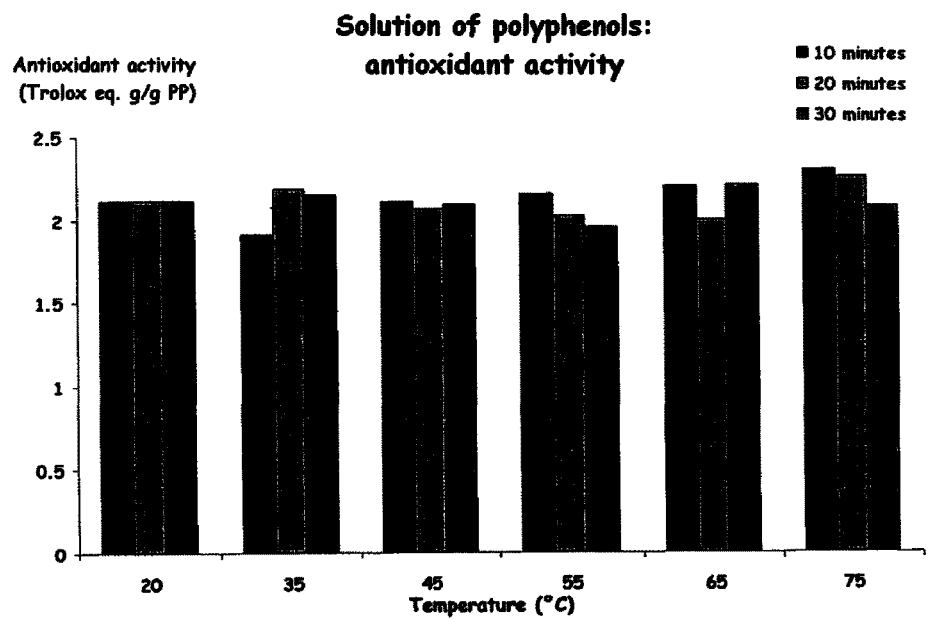

FIG. 4: Change in the antioxidant activity as a function of temperature.

Figure 5:
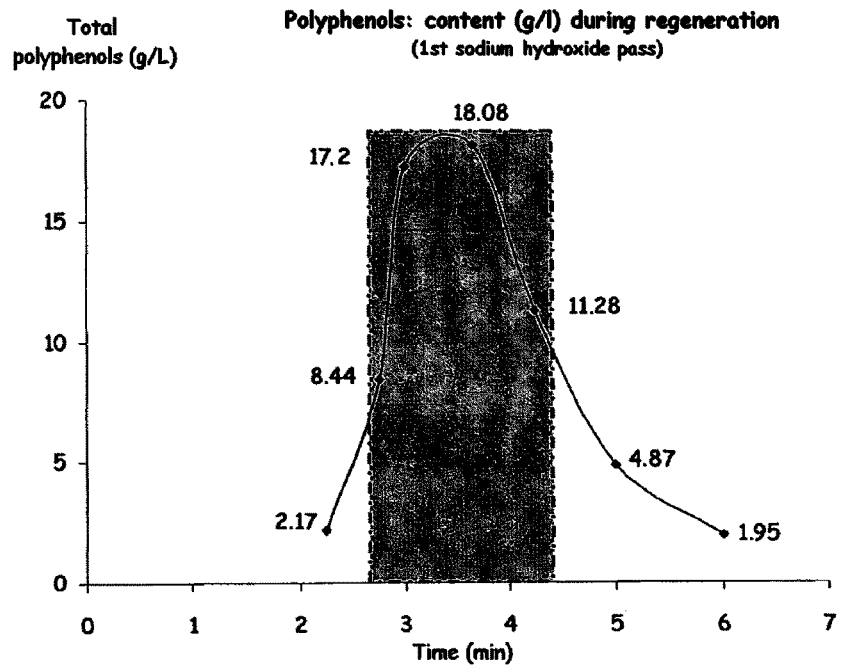

FIG. 5: Change in the polyphenol content during a regeneration.

Figure 6:
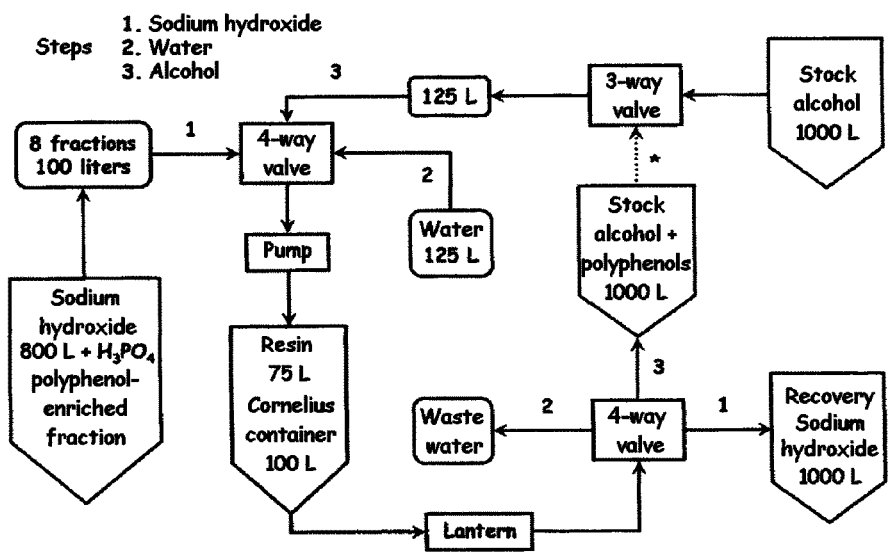

FIG. 6: Pilot test scheme.

Figure 7:
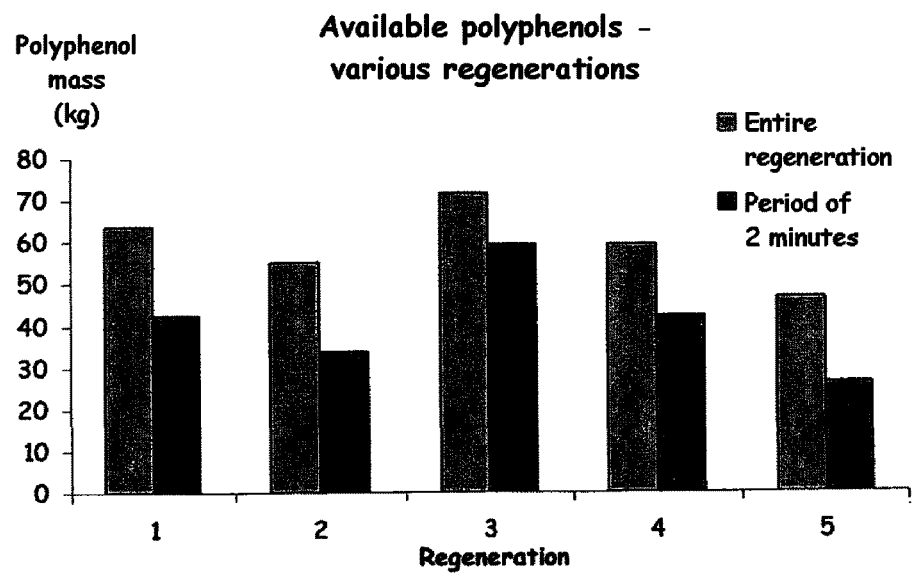

FIG. 7: Polyphenol content during 5 regenerations.

Figure 8:
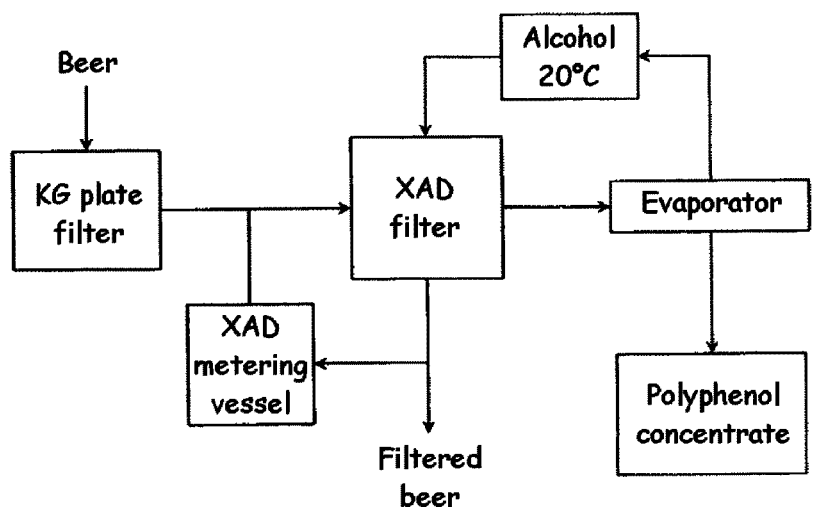

FIG. 8: Scheme of the principle of replacement of PVPP with another resin, XAD.

Figure 9:
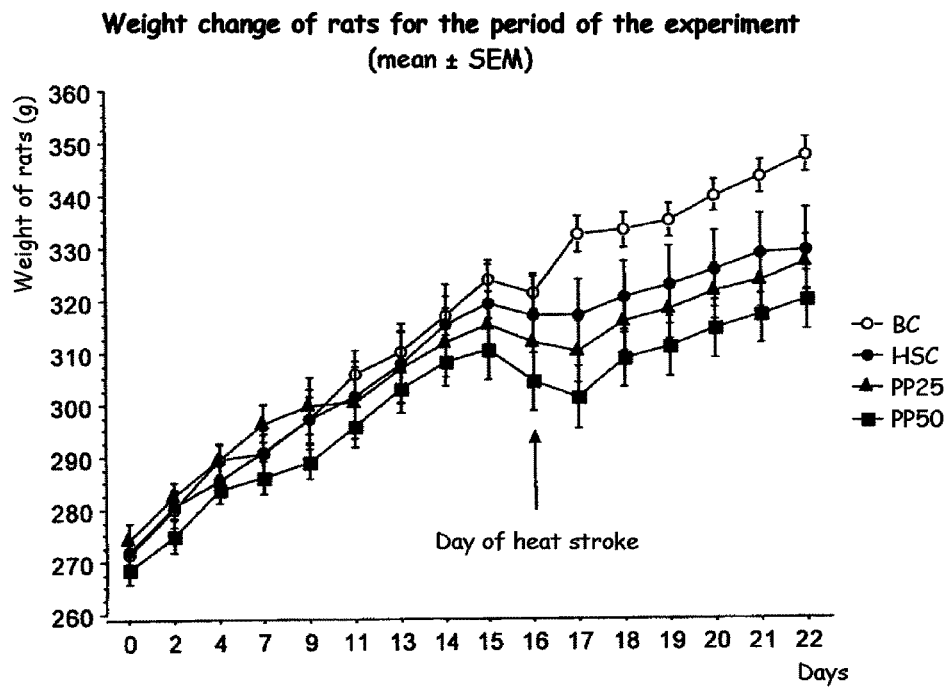

FIG. 9: Weight change in rats during the experimental period (mean±SEM).

Figure 10:
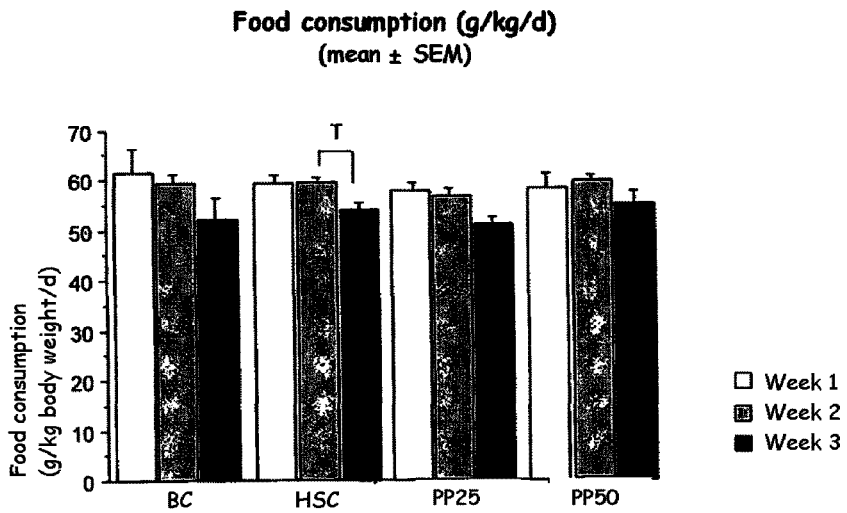

FIG. 10: Food consumption (g/kg/d) (mean±SEM).

Figure 11:
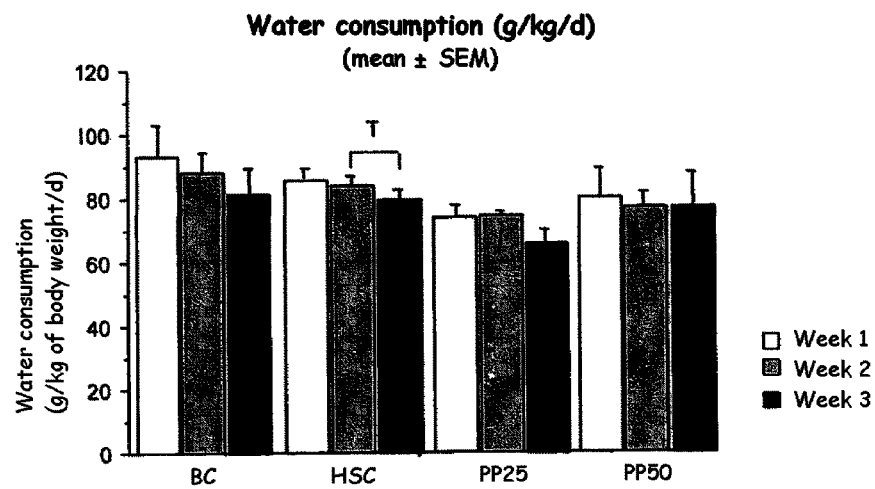

FIG. 11: Water consumption (g/kg/d) (mean±SEM).

Figure 12:
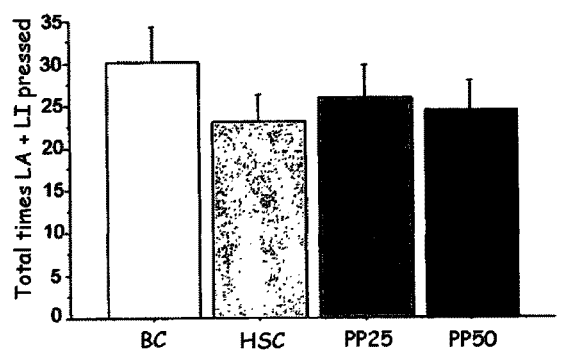

FIG. 12: Total number of times the two levers are pressed during the 10 minutes of the session for becoming accustomed to the test (mean±SEM).

Figure 13:
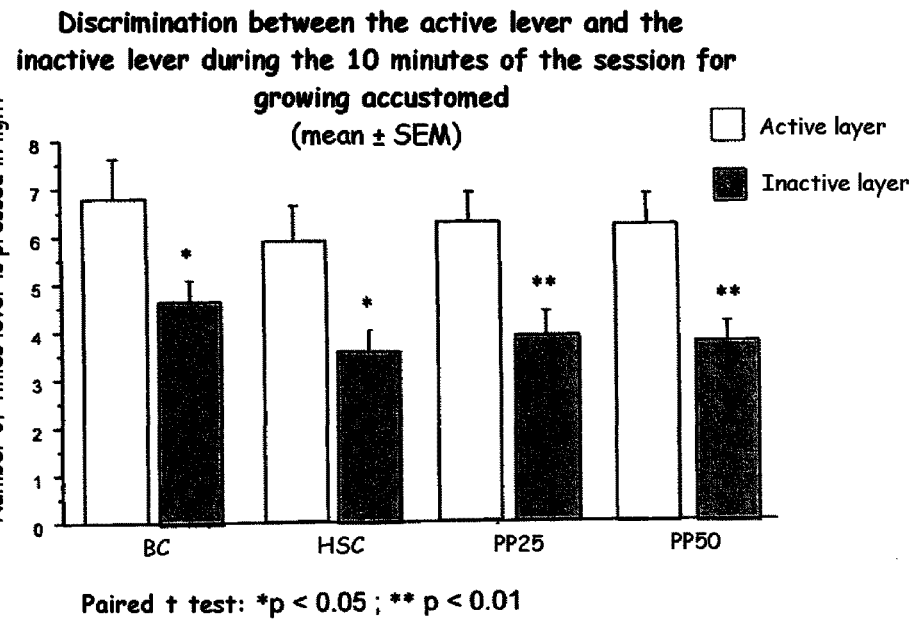

FIG. 13: Discrimination between the active lever and the inactive lever during the 10 minutes of the session for becoming accustomed to the test (mean±SEM).

Figure 14:
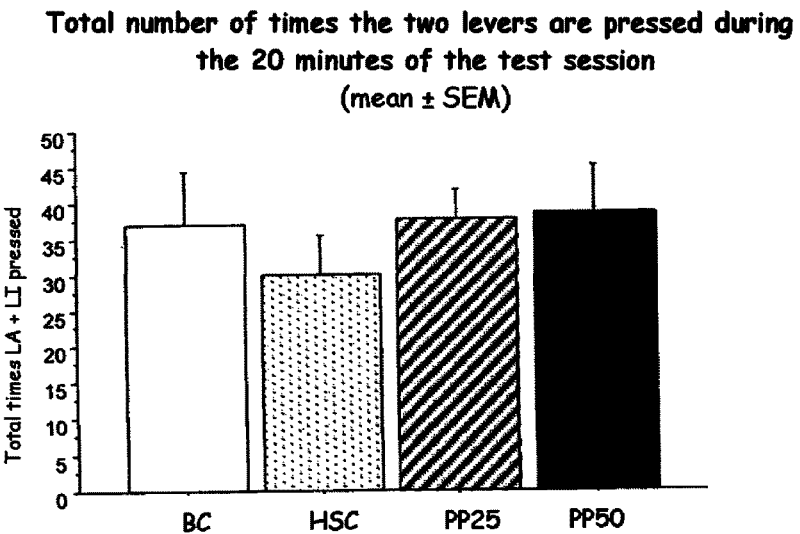

FIG. 14: Total number of times the two levers are pressed during the 20 minutes of the test session (mean±SEM).

Figure 15:
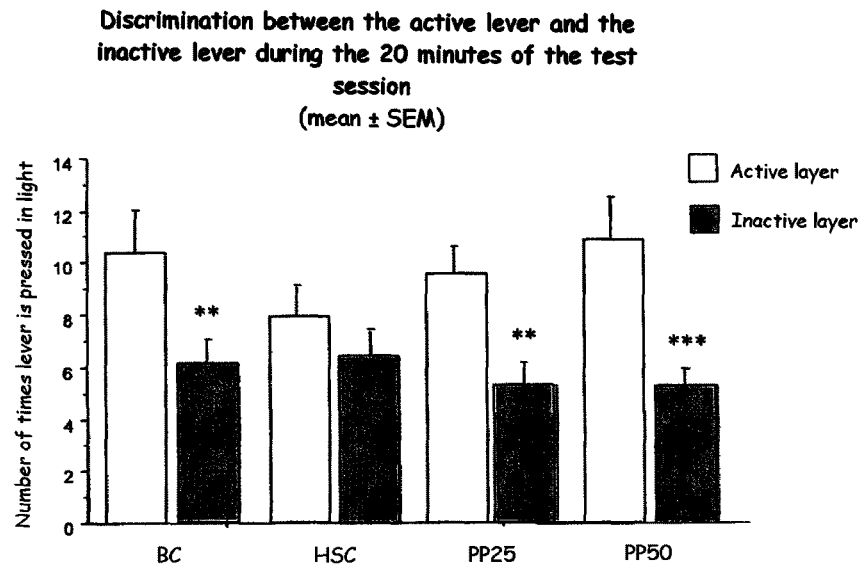

FIG. 15: Discrimination between the active lever and the inactive lever during the 20 minutes of the test session (mean±SEM).

Figure 16:
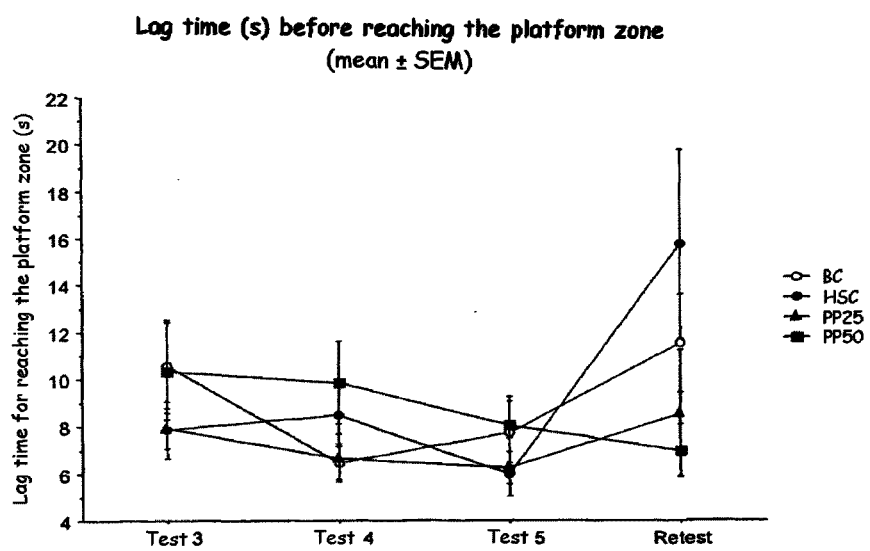

FIG. 16: Lag time (s) before reaching the platform zone (mean±SEM).

Figure 17:
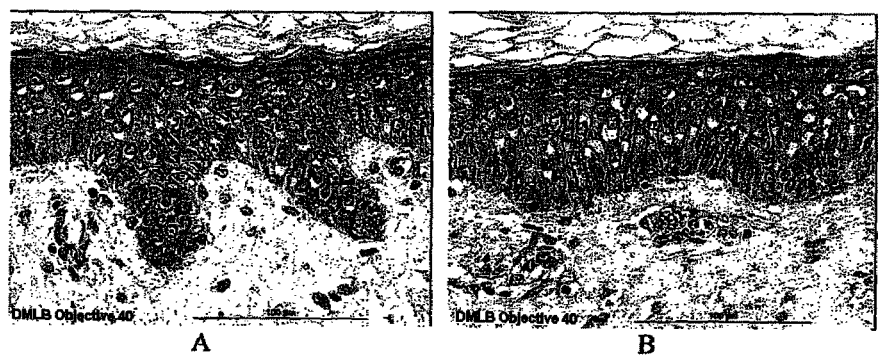

FIG. 17: Microscopic observation of the untreated explants at D0 (A) and D6 (B).

Figure 18:
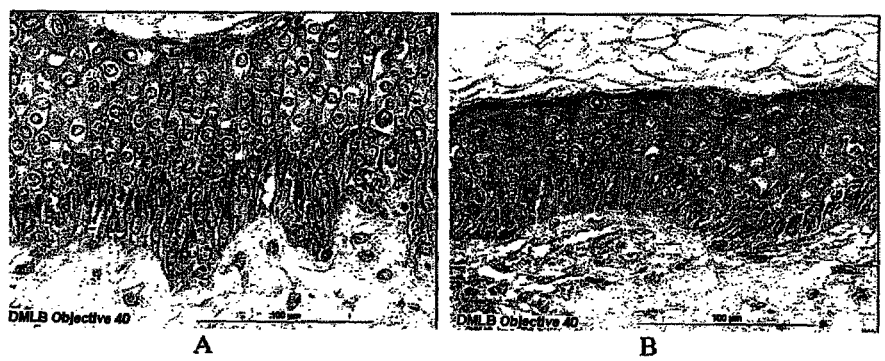

FIG. 18: Microscopic observation of the explants at D6, treated with the formulation containing retinol (A) or with the excipient (B).

Figure 19:
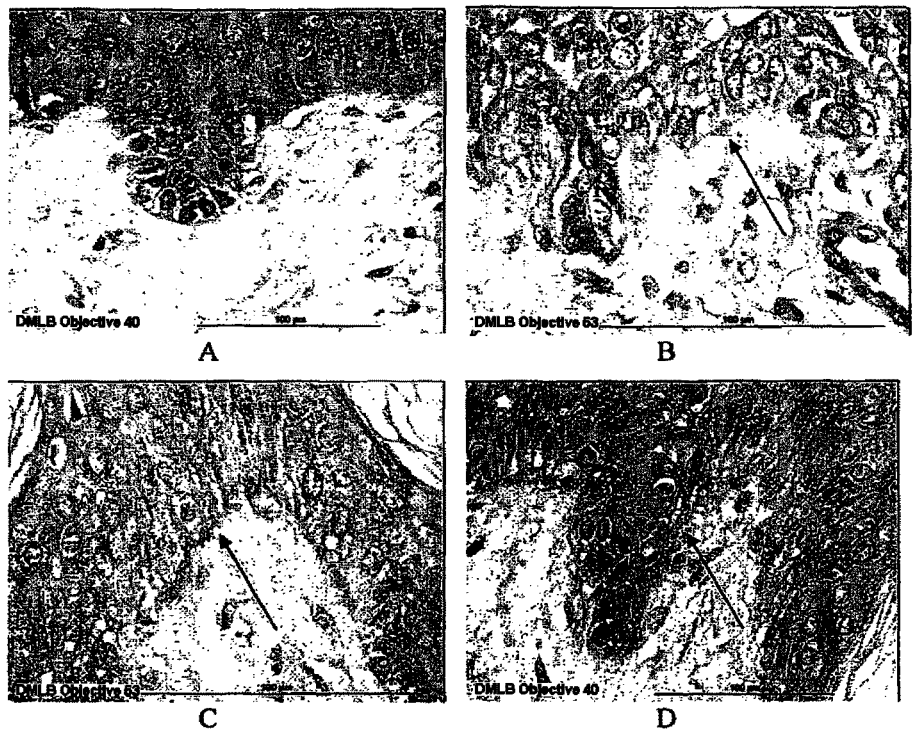

FIG. 19: Microscopic observation at D6 after GAG staining: control (A), reference (B), treated with the polyphenols at 0.5% topically (C), and treated with the polyphenols at 0.025% in the medium.

Figure 20:
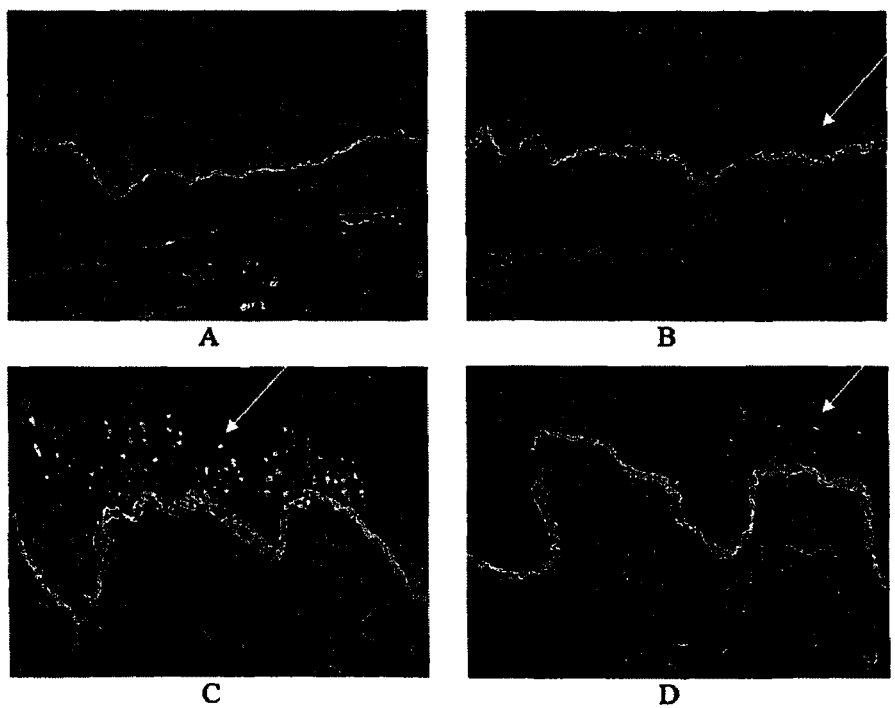

FIG. 20: Microscopic observation at D6, after immunolabeling of laminin-5: control (A), reference (B), treated with the polyphenols at 0.5% topically (C), and treated with the polyphenols at 0.025% in the medium.

Figure 21:
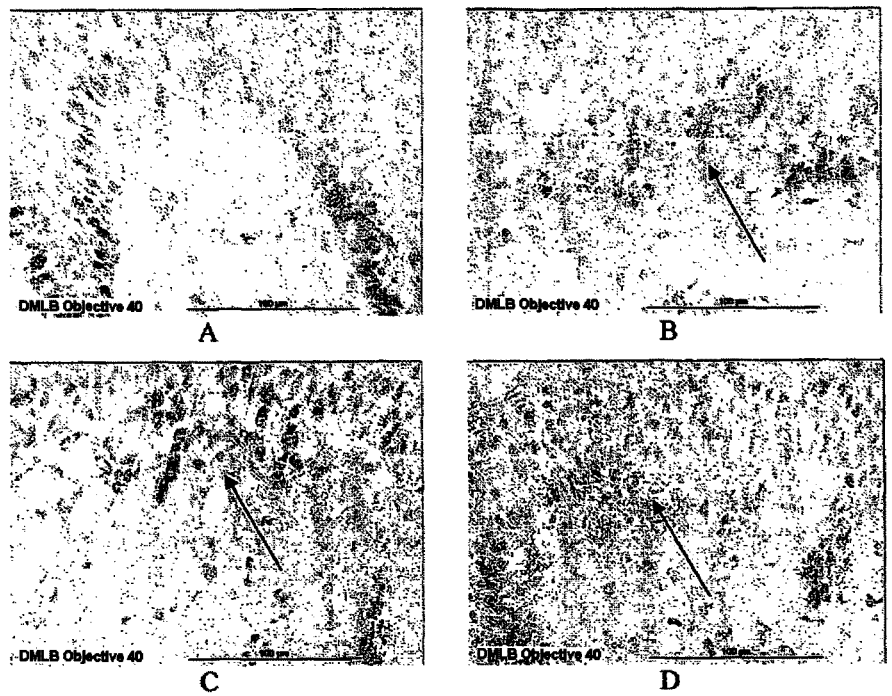

FIG. 21: Microscopic observation at D6, after immunolabeling of collagen III: control (A), reference (B), treated with the polyphenols at 0.5% topically (C), and treated with the polyphenols at 0.025% in the medium.

Figure 22:
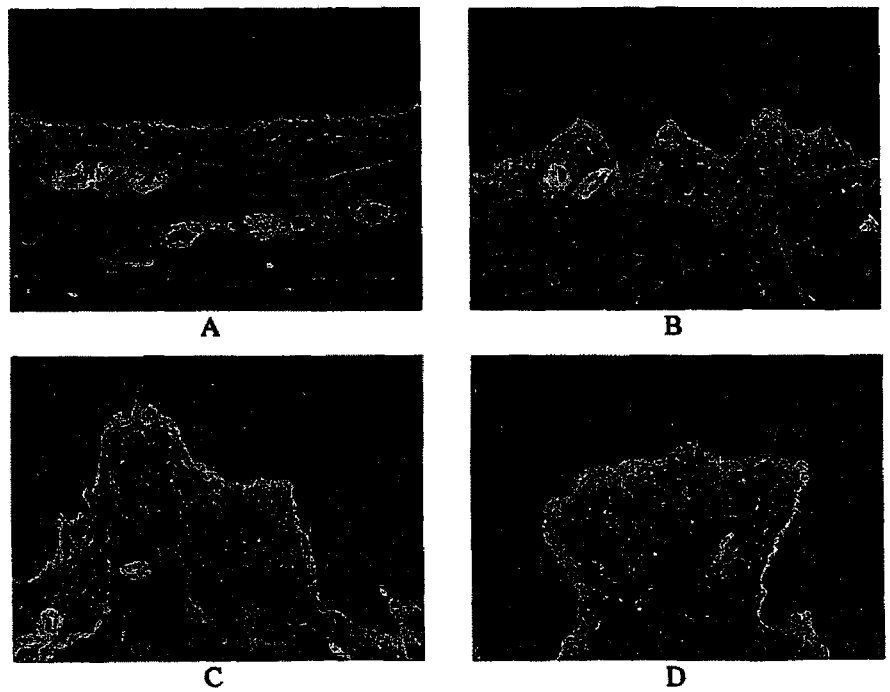

FIG. 22: Microscopic observation at D6, after immunolabeling of collagen IV: control (A), reference (B), treated with the polyphenols at 0.5% topically (C), and treated with the polyphenols at 0.025% in the medium.

Figure 23:
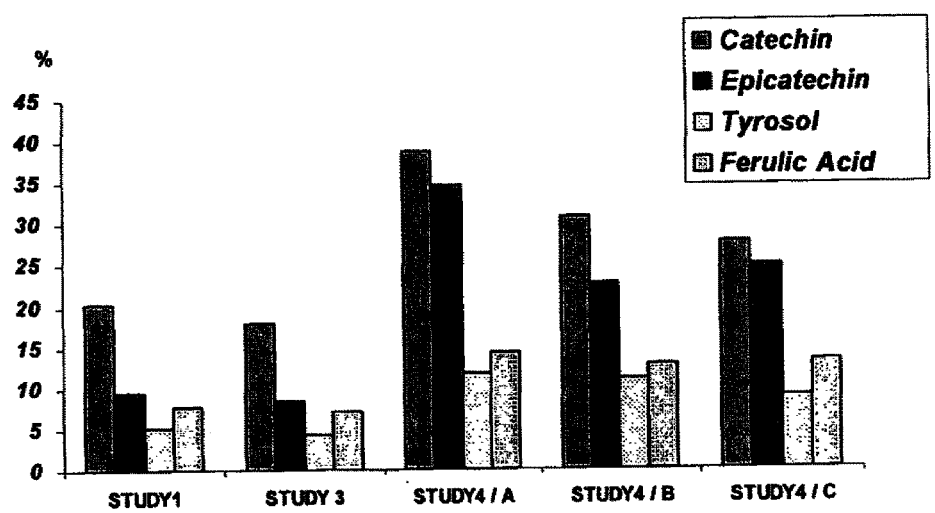

FIG. 23: Flavolol and phenolic acid compositions of the samples (% by mass).

EXAMPLES

Example 1

Laboratory Tests 1.1 Context

The beer filtration process is carried out in two steps:
1. Passing over a Kieselguhr filter and elimination of the residual solid particles ("partially filtered" beer),
2. Decrease of approximately 40% to 50% in the concentration of polyphenols in the beer by means of the PVPP.

The filtered beer is subsequently stored and then packaged.

The PVPP is added to the partially filtered beer as it leaves the Kieselguhr filter. The PVPP adsorbs the polyphenols and is then retained on the PVPP filter. Washing of the filter with hot sodium hydroxide at 1.6% (two portions of 120 hL) makes it possible to remove the polyphenols and to regenerate the PVPP for the next use. The first portion of sodium hydroxide is sent to the purification station, the second is recovered and re-used during the next regeneration. The use and the regeneration of the PVPP are represented in FIG. 1. In the examples which follow, the "regeneration solution" will denote the first portion of sodium hydroxide (Sodium hydroxide 1).

1.2 Stability of the Polyphenols in the Regeneration Solution

The stability of the polyphenols of the regeneration solution is determined under various conditions (pH, time, temperature). The total polyphenols are assayed at various times for each of the conditions, on 5 samples that are taken. Two hours elapsed between the sampling and the first measurement.

FIG. 2 shows the influence of the pH on the preservation of the polyphenols. Over 2 hours, the loss of polyphenols is greater than 55% in the nonacidified sodium hydroxide. The basic solution should be neutralized or acidified immediately as it leaves the PVPP filter in order to be exploitable. The temperature has no influence between 3 and 80° C.

FIG. 3 gives the change in total polyphenols in the regeneration solution over a period of 9 days. The regeneration solution is sampled directly on leaving the PVPP filter. The samples are conditioned and immediately acidified with commercial acid.

The following conditions were tested:
acidity
pH between 2 and 3 for the acidified samples,
pH=13 for the untreated sodium hydroxide samples
nature of the acid used
    phosphoric acid ($H_3PO_4$)
    hydrochloric acid (HCl)
temperature: −20° C., 4° C. or 20° C.
This figure shows that:
1. When the solution is acidified with phosphoric acid, 88% of the polyphenols are preserved up to the 9th day.
2. It is preferable to use phosphoric acid and not hydrochloric acid.
3. The basic solution should be neutralized immediately in order to preserve the polyphenols (already mentioned above).
4. Irrespective of the conditions, the polyphenols undergo a transformation. This phenomenon has been described for the polyphenols in wine (Tubaro et al., 1999). It appears to be a dimerization of the polyphenols (Brouillard et al., 1997).
5. The influence of the temperature (4° C. as compared with 20° C.) is very small.

The influence of temperature on the stability of the polyphenols was subsequently measured through the antioxidant activity of a solution of polyphenols (FIG. 4). Samples of the same solution were kept at various temperatures (between 35 and 75° C.) for 10, 20 or 30 minutes. The antioxidant activity was measured by the DPPH method (Brand-Williams et al., 1995).

FIG. 4 shows that:
1. The antioxidant activity (2.11 g Trolox eq/g polyphenols) is stable between 20 and 75° C.
2. The variations observed (±5%) are related to experimental variations and are not significant.
NB: These results were confirmed on the pilot batch between 40 and 70° C.

1.3 Laboratory Production of Polyphenol-Enriched Extracts

In order to determine the phenolic composition of beer, McMurrough et al. carried out an extraction with ethyl acetate on degassed beer and then analyzed the extract by HPLC (McMurrough et al., 1984). A first extraction was carried out by this technique, in order to extract the polyphenols of the regeneration solution.

The polyphenols were therefore extracted from the PVPP-regeneration sodium hydroxide solution by applying the following protocol:
1. acidification of the sodium hydroxide solution to pH 2 with HCl,
2. addition of ethyl acetate (sodium hydroxide/ethyl acetate ratio: 1/1.5, v/v),
3. stirring for 2 hours, speed 300-500 rpm, then left to stand for 2 hours and phase separation,
4. recovery of the organic phase, evaporation and freeze-drying.

The characteristics of the extracts obtained are summarized in table 2 (column A).

The previous method makes it possible to obtain polyphenols with a purity of 77%. The extraction yield is, on the other hand, low (approximately 37%). Other conditions were tested in order to increase the extraction yield. The modification related to:
the pH (between 1 and 7),
the extraction solvent (ether, dichloromethane),
the addition of sodium chloride in order to improve the separation of the organic and aqueous phases.

The characteristics of the extracts obtained are summarized in table 2 (column B). Overall, when these variants were used, the extraction yield changed to 32%. The extracts obtained contain more salts than previously and the polyphenol titer was only 42%. The different variants did not therefore make it possible to improve the efficiency of the extraction technique.

In order to develop a method for recovering the polyphenols in greater amount under conditions more compatible with an industrial exploitation suitable for existing plants and with the applications envisioned, other techniques for desalifying and concentrating the polyphenols were envisioned. These possibilities are summarized in table 1.

TABLE 1

Proposed methods for concentrating and desalifying

| Task | Method | Miscellaneous information |
| --- | --- | --- |
| Acidification (rapidly, on leaving the PVPP filter) and desalification | Direct acidification | Generation of salts Salt elimination required |
|  | Cationic exchange resin | No additional desalification step Regeneration of the resin with acid (HCl, $H_2SO_4$) |
| Concentration | Membrane filtration | Elimination of a part of the water, concentration by a factor of 5 Pressure 40-50 bar |
|  | Adsorption of polyphenols on to resin | Regeneration with alcohol Distillation under reduced pressure |

The choice concentrated on a polyphenol adsorption resin developed by the company Rohm & Haas. The polyphenols were therefore extracted from the neutralized PVPP-regeneration sodium hydroxide by applying the following method.
1. Passing of the sodium hydroxide solution through a column containing the XAD1180 resin and adsorption of the polyphenols. The adsorption capacity of the resin is 20 g of polyphenols per liter of resin,
2. washing of the resin with water in order to remove the traces of salts and other impurities,
3. elution of the polyphenols with ethanol,
4. recovery of the organic phase, evaporation and freeze-drying.

150 ml of water and 150 ml of alcohol were used per 100 ml of resin.

The characteristics of the extracts obtained are summarized in table 2 (column C).

This method solves the problems associated with the use of ethyl acetate.

The extraction of the available polyphenols is increased (65% extraction), the purity of the extracts increases to 85-90%, ethanol is used or present in many industrial processes (pharmacy) or commonly consumed products (beer, antitussives).

1.4 Polyphenol Extracts Obtained in the Laboratory

The characteristics of the extracts obtained in the laboratory by means of the three methods described above are summarized in table 2 below.

TABLE 2

Comparison of the extracts obtained by various methods on various samples

| | Batch | | |
|---|---|---|---|
| | A | B | C |
| Method | Ethyl acetate | Variants | Resin + alcohol |
| Amount of dry matter obtained (g) | 9.3 | 29.6 | 17.5 |
| Polyphenol titer (g/g DM) | 0.77 | 0.42 | 0.85 |
| Mass polyphenols (g) | 7.2 | 12.4 | 14.9 |
| Available polyphenol extraction yield (%) | 37 | 32 | 65 |
| Antioxidant activity | | | |
| mg DPPH/g DM | 2.5-3.0 | 1.2-1.5 | 3.7-4.5 |
| mg DPPH/g polyphenols | 3.2-3.9 | 2.8-3.6 | 4.4-5.3 |
| Trolox equivalence (g/g DM) | 1.08-1.31 | 0.50-0.67 | 1.62-1.96 |
| Trolox equivalence (g/g polyphenols) | 1.4-1.7 | 1.2-1.6 | 1.9-2.3 |

Example 2

Scale-Up, from Laboratory to Production 2.1 Pilot Test

Samples taken show that, during the regeneration of the PVPP, only the first wash with sodium hydroxide is rich in polyphenols. In addition, the concentration of polyphenols varies during the PVPP generation. It is represented for one regeneration in FIG. 5.

The amount of polyphenols is evaluated by integrating the surface area under the curve. According to the appearance of the curve, approximately 65% of the polyphenols contained in the regeneration solution are removed during a period of 2 minutes (shaded part on FIG. 5). Consequently, during this time period, approximately 10 hL of sodium hydroxide were sampled for carrying out the pilot test.

The validation of the proposed method required that a pilot test be carried out in order to produce approximately 5 to 10 kg of polyphenols.

The sodium hydroxide sample was taken directly on leaving the PVPP filter after suspension of the standard regeneration sequence at the 3rd minute (FIG. 5, shaded part). The solution was acidified immediately with 20 liters of phosphoric acid during the filling of the vessel used for transport.

The polyphenol content of the sampled sodium hydroxide (800 l) was 19 g/l. The acidified sodium hydroxide ($H_3PO_4$, pH 5) was treated in portions of approximately 100 liters. The apparatus used is shown schematically in FIG. 6.

A variant of this apparatus consists in recirculating the organic solvent (dotted arrow marked with a star *). In this case, the volume of organic solvent can be reduced. Thus, for example, 100 l of alcohol can be used instead of 1000 l, as indicated in FIG. 6. This variant has several advantages: (i) the polyphenols can be obtained at higher concentrations; (ii) the evaporation becomes optional, or even needless, and it is possible to do without an evaporator (this is also true in the version where a single resin is used, as illustrated in FIG. 8); (iii) the elimination of the evaporation step, resulting in direct freeze-drying of the product, makes the process more economical.

A metal filter was placed in the Cornelius container and the circulation of the fluid was forced from the bottom to the top in order to avoid problems of clogging-up.

The extraction yield of 60%, can be increased by improving the sodium hydroxide solution treatment conditions.

The amount of polyphenols isolated was approximately 9 kg and the purity was greater than 80%. The antioxidant activity of the product obtained was higher than in the laboratory tests since the implementation of the pilot made it possible to avoid air entering the circuit during the shifting between the various liquids, and therefore degradation of the polyphenols.

TABLE 3

Comparison of the extracts obtained by the method selected

| | Batch | |
|---|---|---|
| | Lab | Pilot |
| Amount of dry matter (obtained in the lab, calculated for the pilot) | 17.5 g | 10.96 kg |
| Polyphenol titer (g/g DM) | 0.85 | 0.81 |
| Mass polyphenols | 14.9 g | 8.82 kg |
| Available polyphenol extraction yield (%) | 65 | 60 |
| Antioxidant activity | | |
| mg DPPH/g DM | 3.7-4.5 | 5.3 |
| mg DPPH/g polyphenols | 4.4-5.3 | 6.6 |
| Trolox equivalence (g/g DM) | 1.62-1.96 | 2.24 |
| Trolox equivalence (g/g polyphenols) | 1.9-2.3 | 2.8 |

2.2 Industrial Aspects

In order to verify the reproducibility of the results obtained above, these operations were repeated for five regenerations (FIG. 7).

Owing to industrial constraints, regeneration 5 was carried out although only 75% of the available PVPP was used and the amounts of polyphenols determined are lower.

The sodium hydroxide samples taken on the various PVPP filters show similar characteristics (table 4):

the available polyphenol potential is approximately 55 to 65 kg per regeneration, according to the appearance of the curve, 65% of the polyphenols contained in the regeneration solution are concentrated over a period of 2 minutes (shaded area on FIG. 5).

TABLE 4

Data characterizing a regeneration

|  | Passing of sodium hydroxide 1 | Period retained | Proportion (%) |
|---|---|---|---|
| Duration (minutes) | 7 | ~2 | 25-30 |
| Volume of sodium hydroxide (hL) | 120 | ~35 | 25-30 |
| Available polyphenols (kg) | 55-65 | 35-45 | 60-65 |

Example 3

Variation for the Recovering of Polyphenols Resulting from Beer

A second possibility for recovering the polyphenols consists in replacing the PVPP with the resin developed by Rohm & Haas (FIG. 8). Since the desorption of this resin is carried out using alcohol, the salts come only from the beer and not from the sodium hydroxide neutralized with acid (zero consumption of sodium hydroxide and of acid). It is possible to propose a product having a minimum polyphenol titer of 95%. In addition to the purity, the amount of recoverable polyphenols increases, and reaches 60 kg per regeneration. In order to be implemented industrially, this variation requires a modification of the list of technological auxiliaries permitted in the treatment of beer, and also a development study in order to verify the impact of these modifications on the physical and organoleptic characteristics of the beer.

Example 4

Study of the Preventive Effects of Polyphenols Resulting from the Co-Products of the Brewing Industry on Antioxidant Activity and on the Cognitive Sphere Following a Heat Stroke in Adult Male Sprague Dawley Rats 4.1 Introduction The preventive effects of polyphenols resulting from the co-products of the brewing industry, on antioxidant activity and also on the cognitive sphere following a heat stroke, were evaluated in adult male Sprague Dawley rats.

The animals of the various groups were treated for three weeks (D1 to D22) with the polyphenols administered orally at the doses of 25 and 50 mg/kg, or with the vehicle (spring water). The antioxidant activity of the polyphenols was evaluated on whole blood at the beginning and at the end of preventive treatment, and then the day after the heat stroke carried out on day 16. The learning tests were carried out both in the aversive light stimulus avoidance conditioning model (effecting conditioning) on day 19 and in the Morris water maze test (spatial memory) on days 21 and 22, in order to evaluate the protective effects of the polyphenols against the cognitive deficits induced by excessive production of free radicals following the heat stroke.

4.2 Materials and Methods

Animals

Sixty-four male Sprague Dawley rats (Harlan, Holland) weighing 250 to 275 g were used. Upon reception, the rats were labeled and divided up into groups of four in F type polycarbonate cages (48×27×20 cm, U.A.R., 91—Epinay-Sur-Orge, France). The animals were housed in an air-conditioned animal house at a temperature of $22\pm1°$ C. The rats had conventional feed 2016 (Harlan, France) and drink ad libitum and were subjected to a 12-hour inverted light-dark cycle.

After familiarization with the laboratory conditions for one week, the rats were weighed and randomly divided up into four treatment groups (n=16 rats/group):
"BC" group: blank control treated with the vehicle and not subjected to heat stroke;
"HSC" group: heat stroke control treated with the vehicle and subjected to the heat stroke;
"PP25" group: treated at the dose of 25 mg/kg of polyphenols and subjected to the heat stroke;
"PP50" group: treated at the dose of 50 mg/kg of polyphenols and subjected to the heat stroke.

In order to avoid possible interferences between the various products, the rats in the same cage all received the same treatment. The rats of the various groups were handled in the same way and under the same conditions.

Administration of the Products and of the Tests (Table 5)

The polyphenols, solubilized in spring water (5 ml/kg) at the doses of 25 and 50 mg/kg, and the vehicle were administered intragastrically to the animals each day for three weeks. Following delivery of the treatment, the animals of all the groups were fed ad libitum with the standard diet.

Samples of five hundred microliters of whole blood were taken from 12 rats per group on D0 and on D15 in order to evaluate the antioxidant activity of the polyphenols. The samples were taken from the caudal vein using a needle, and the blood was directly collected in an EDTA tube. This method makes it possible to collect small volumes of blood without sacrificing the animal. A session for becoming accustomed to the aversive light stimulus avoidance conditioning test (ALSAT) device was carried out for 10 minutes on D15 in order to compare the manipulatory activity of the animals of the four groups. A heat stroke was performed on D16 and a further blood sample was taken on D17 in order to evaluate the protective effects of the polyphenols against the excess production of free radicals and to verify the antioxidant activity in the animals having previously ingested the product. Three days after the heat stroke (D19) the animals were tested in the ALSAT in order to evaluate their learning performance levels as a function of the products ingested. On days 21 and 22, the rats were tested in the Morris water maze in order to evaluate their acquisition of spatial learning and their short-term and long-term memory.

The animals were weighed every second day in order to adjust the amount of polyphenols to be administered to them daily as a function of their body weights.

The food and water intakes of the animals were recorded during the two weeks preceding the heat stroke and the week following it.

TABLE 5

Product and test administration protocol

| Groups | n | Treatment (D1 to D22) | Dose mg/kg/d | Heat stroke (HS) (n = 16) | Antioxidant activity measurement (n = 12) | Becoming accustomed ALSAT | ALSAT Test | Morris Test |
|---|---|---|---|---|---|---|---|---|
| BC | 16 | Spring water | — | No | Day 0, D15 and D17 | D15 | D19 | D21 and D22 |

TABLE 5-continued

Product and test administration protocol

| Groups | n | Treatment (D1 to D22) | Dose mg/kg/d | Heat stroke (HS) (n = 16) | Antioxidant activity measurement (n = 12) | Becoming accustomed ALSAT | ALSAT Test | Morris Test |
|---|---|---|---|---|---|---|---|---|
| HSC | 16 | Spring water | — | D16 | | | | |
| PP25 | 16 | Polyphenols | 25 | D16 | | | | |
| PP50 | 16 | Polyphenols | 50 | D16 | | | | |

Experimental Procedures

Justification of the Heat Stroke Model

Experimental heat stroke reproduces the effects of prolonged exposure to heat. Various animal models of heat stroke exist, the most widespread being the murine model.

In anesthetized rats exposed to heat, there is a terminal cerebral ischemia phenomenon with a strong release of dopamine, serotonin, glutamate and nitrogen monoxide (Yang and Lin, 2002; Canini et al., 2001). It is therefore not surprising to find, at that moment, an increase in membrane peroxidation markers and brain lesions.

In awake rats exposed to heat (Tdb=40° C.), it is impossible, for ethical reasons, to go as far as terminal ischemia. Nevertheless, it is possible to follow the three-phase change in the central temperature: immediately after the beginning of exposure, the temperature increases and then stabilizes in a thermoregulation plateau which ends with body temperature increasing and continues until death of the animal. Interruption of the exposure at a body temperature of 41.5-42.0° C. is then a good compromise: the animals are in the final phase of increasing body temperature and the survival rate is high (about 80%).

In this context, behavioral alterations of the manipulatory hyperactivity and cognitive deficit type were evaluated a few days after heat stroke exposure in the aversive light stimulus avoidance conditioning test and in the Morris water maze test.

Heat Stroke

After having taken the initial rectal temperature of the rat, the animal was placed at 40° C. in the heat stroke device. When the body temperature of the rat reached 41.5° C., it was removed from the device and put back in its cage.

Antioxidant Activity

The antioxidant activity was measured using the KRL test (Kirial International, France) (Prost et al, 1992). It consists in subjecting a blood sample to free-radical attack under controlled and standardized conditions. All the enzyme and chemical systems of the sample mobilize to protect the integrity of the cells until said cells are lysed. Measuring the decrease in absorbance makes it possible to follow the gradual disappearance of the cells. The resistance of the blood to free-radical attack is expressed by the time necessary for lysis of 50% of the blood cells (half-hemolysis time).

The test was carried out using the KRL kit (Reference KRLSPI101/103/105) in 96-well microplates and the results were analyzed with the KRL software (version 3.02).

Whole-blood analysis makes it possible to measure the intracellular and extracellular defenses, which gives an instantaneous indication of the physiological condition of the rat at the time the blood sample was taken.

Aversive Light Stimulus Avoidance Conditioning Test (ALSAT)

This model uses the aversion of the rat to a strongly illuminated environment. Firstly, the rat learns to control its aversive light environment in the context of avoidance conditioning: the animal learns to press on an active lever in order to obtain periods of darkness as positive reinforcement (Messaoudi et al, 1996; Messaoudi et al, 1999).

The experimental device consists of a strongly illuminated (1200 lux) isolated cage (50×40×37 cm), comprising two levers: one is active, making it possible to obtain 30 seconds of darkness as positive reinforcement when it is actuated, and the other is inactive. Pressing on the active lever during the period of darkness does not provide additional periods of darkness.

The test battery, composed of four conditioning devices, is entirely automated and computer-controlled. A session for becoming accustomed to this device was carried out the day before the heat stroke on D15. On the day of the test (D19) the procedure for acquisition of discriminating learning was carried out over a period of 20 minutes, three days after the heat stroke.

The variables recorded were the number of times the active lever (LA) and the inactive lever (LI) were pressed and also the number of periods of darkness obtained.

The numbers of times the active and inactive levers were pressed made it possible to evaluate the level of the manipulatory activity. The acquisition of learning (discrimination between the two levers) was evaluated by comparing the cumulative number of times each of the two levers were pressed (LA compared to LI).

Morris Water Maze Test: Spatial Memory

The rat, placed in a circular bowl (Ø 150 cm) filled with water, swims and seeks to flee the aversive water medium by taking refuge on a platform immersed 2 mm under the surface of the water. The test session comprises 5 consecutive trials during which the animal learns to locate the position of the immersed platform and to take refuge on it. A resting time of 30 seconds on the platform is observed between two trials in order to allow the rat to find its spatial bearings, essential to its orientation in the device.

The following day, the rat is again placed under the same experimental conditions and a single trial is carried out (retest).

This test made it possible, on day 21, to evaluate the exploratory and cognitive performance levels in the progressive spatial learning situation (short-term memory), and, during the retest (D22) to evaluate the long-term memory of the rat.

The variable studied is the lag time before the position of the immersed platform is reached (Blokland et al., 2004; Morris et al., 1982).

Statistical Analysis

Depending on the Gaussian distribution or non-Gaussian distribution of the data, parametric (P) or non-parametric (NP) statistical tests were used: factorial measures analysis of variance (ANOVA) (P) or Kruskal-Wallis test (NP), followed, where appropriate by the unpaired t test (P) or the Mann-Whitney test (NP) for comparing the treated groups with the control group. For the analysis of repeated or paired measurements, repeated measures ANOVA (P) or the Friedman test (NP) were used, followed, where appropriate, by paired comparison tests: paired t test (P) or Wilcoxon test (NP).

The statistical treatments were carried out using the Statview 5 software (SAS Institute Inc.).

4.3. Results

Comment: during this study, three rats died before the end of the experiment.

Weight Change

From day 0 to day 16, the analysis of variance did not show any significant heterogeneity among the weights of the rats of the various groups.

From day 17 to day 22, the analysis of variance showed a significant heterogeneity among the weights of the rats of the various groups (table 6).

The unpaired t test showed that, on days 17 and 22, the weights of the rats of the HSC group were significantly lower than those of the rats, of the BC group. On days 18, 20 and 21, the weights of the rats of the HSC group showed a tendency to be lower than those of the rats of the BC group.

From day 17 to day 22, the weights of the rats of the PP25 and PP50 groups were significantly lower than those of the rats of the BC group.

The weight of the rats of the PP25 and PP50 groups were not significantly different from those of the rats of the HSC group, with the exception of day 17, where the weights of the rats of the PP50 group showed a tendency to be lower than those of the rats of the HSC group (table 7; FIG. 9).

PP25 and PP50 groups after the heat stroke, the weight changes in the rats of these groups were similar.

The repeated measures ANOVA applied to the weight change in the rats of each of the four groups between D17 and D20 showed a significant heterogeneity after the heat stroke (table 8).

TABLE 8

Comparison of the weights of the rats of the various groups between D17 and D20

| Groups | BC (n = 16) | HSC (n = 15) | PP25 (n = 15) | PP50 (n = 15) |
|---|---|---|---|---|
| Repeated measures ANOVA from D17 to D20 | F = 20.22 $P < 0.0001$ | F = 6.21 $P < 0.01$ | F = 47.68 $P < 0.0001$ | F = 4.83 $P < 0.01$ |

The comparison between D17 and D18 using the paired t test showed a significant increase in the weights of the rats of the PP25 (t=5.97, p<0.0001) and PP50 (t=7.62, p<0.0001) groups. No significant difference was observed for the weights of the rats of the BC (t=0.77, p=0.45) and HSC (t=1.26, p=0.23) groups.

The comparison between D18 and D19 showed a significant increase in the weights of the rats of the PP25 (t=3.06, p=0.008) and PP50 (t=2.97, p=0.010) groups, and a tendency

TABLE 6

Analysis of variance of the weights of the rats of the four treatment groups

| | Days | | | | | | | | | | | | | | | |
|---|---|---|---|---|---|---|---|---|---|---|---|---|---|---|---|---|
| | 0 | 2 | 4 | 7 | 9 | 11 | 13 | 14 | 15 | 16 | 17 | 18 | 19 | 20 | 21 | 22 |
| ANOVA: $F_{(3,57)}$ Significance | 0.74 N.S. | 1.05 N.S. | 0.95 N.S. | 1.27 N.S. | 0.93 N.S. | 0.50 N.S. | 0.27 N.S. | 0.47 N.S. | 0.93 N.S. | 1.57 N.S. | 5.63 $P < 0.01$ | 3.76 $P < 0.05$ | 3.38 $P < 0.05$ | 3.94 $P < 0.05$ | 4.12 $P < 0.05$ | 4.41 $P < 0.01$ |

TABLE 7

Transverse comparison of the weights of the rats of the various groups (unpaired t test)

| | Days | | | | | |
|---|---|---|---|---|---|---|
| | 17 | 18 | 19 | 20 | 21 | 22 |
| HSC vs. BC | t = 2.07 $P < 0.05$ | t = 1.73 $P < 0.10$ | t = 1.57 N.S. | t = 1.82 $P < 0.10$ | t = 1.80 $P < 0.10$ | t = 2.14 $P < 0.05$ |
| PP25 vs. BC | t = 3.32 $P < 0.05$ | t = 2.70 $P < 0.05$ | t = 2.76 $P < 0.01$ | t = 3.04 $P < 0.01$ | t = 3.28 $P < 0.01$ | t = 3.45 $P < 0.01$ |
| PP50 vs. BC | t = 4.61 $P < 0.0001$ | t = 3.94 $P < 0.001$ | t = 3.79 $P < 0.001$ | t = 4.03 $P < 0.001$ | t = 4.20 $P < 0.001$ | t = 4.32 $P < 0.001$ |
| PP25 vs. HSC | t = 0.77 N.S. | t = 0.52 N.S. | t = 0.51 N.S. | t = 0.47 N.S. | t = 0.54 N.S. | t = 0.26 N.S. |
| PP50 vs. HSC | t = 1.74 $P < 0.010$ | t = 1.35 N.S. | t = 1.26 N.S. | t = 1.24 N.S. | t = 1.22 N.S. | t = 0.99 N.S. |

Interpretation: after 15 days of treatment with the polyphenols at the doses of 25 and 50 mg/kg, the weight change of the groups treated with the polyphenols followed that of the rats of the control group. No toxic effect, of the polyphenols was noted.

The heat stroke led to a significant weight loss in the HSC, PP25 and PP50 groups compared with the BC control. There was no significant difference between the HSC group and the toward an increase in the weight of the rats of the BC group (t=1.93, p=0.073). No significant difference was observed for the weight of the rats of the HSC group (t=0.94, p=0.365).

The comparison between D19 and D20 showed a significant increase in the weights of the rats of the BC (t=6.48, p<0.0001), HSC (t=4.69, p=0.0003) and PP25 (t=4.75, p=0.0003) groups. No significant difference was observed for the weight of the rats of the PP50 group (t=0.68, p=0.507).

Interpretation: the BC rats followed a conventional weight-gain curve after the fasting on the day of the heat stroke, whereas the rats treated with the polyphenols re-gained weight from the day after the heat stroke, this being the case for three consecutive days for the PP25 group and two days for the PP50 group; the rats of the HSC group only began to re-gain weight on the third day after the heat stroke (D19).

Food Intake

The heat stroke was administered to the animals at the beginning of week 3.

The Kruskal-Wallis test showed no significant heterogeneity for the food consumptions by the rats of the BC, HSC, PP25 and PP50 groups during weeks 1, 2 and 3.

The repeated measures analysis using the Friedman test showed a significant heterogeneity for food consumption during weeks 1, 2 and 3 for the rats of the HSC group ($\chi^2$=6; ddl=2; p=0.05). The food consumption by the rats of the HSC group showed a tendency to decrease between week 2 and week 3 (Wilcoxon test: z=1.826; p=0.068) (table 9; FIG. 10).

TABLE 9

Comparison of food consumption by the rats of the various groups (g/kg/d); (mean ± SEM)

| | BC (n = 4) | HSC (n = 4) | PP25 (n = 4) | PP50 (n = 4) | Kruskal-Wallis unpaired analysis |
|---|---|---|---|---|---|
| Week 1 | 61.80 ± 4.58 | 59.33 ± 1.28 | 58.15 ± 0.88 | 58.40 ± 3.19 | H = 1.853 ddl = 3; N.S. |
| Week 2 | 59.36 ± 1.97 | 59.93 ± 0.49 | 58.82 ± 1.34 | 59.25 ± 0.91 | H = 2.934 ddl = 3; N.S. |
| Week 3 | 52.29 ± 4.13 | 54.08 ± 1.49 | 50.93 ± 1.75 | 55.10 ± 2.33 | H = 1.588 ddl = 3; N.S. |
| Friedman test | $\chi^2$ = 4.50 ddl = 2 N.S. | $\chi^2$ = 6.00 ddl = 2 p < 0.05 | $\chi^2$ = 4.50 ddl = 2 N.S. | $\chi^2$ = 3.50 ddl = 2 N.S. | — |
| Wilcoxon test Week 1 vs. Week 2 | — | z = 0 N.S. | — | — | — |
| Week 2 vs. Week 3 | — | z = 1.826 p < 0.10 | — | — | — |

Interpretation: the rats of the HSC group showed a tendency to consume less food after the heat stroke than during the first two weeks of the study.

Water Consumption

The Kruskal-Wallis test did not show any significant heterogeneity for the water consumptions of the various groups during weeks 1, 2 and 3.

The Friedman test demonstrated a significant difference for the water consumption during weeks 1, 2 and 3 for the rats of the HSC group ($\chi^2$=6.50; ddl=2; p=0.039). The water consumption by the rats of the HSC group showed a tendency to decrease between week 2 and week 3 (Wilcoxon test: z=1.83; p=0.68) (table 10, FIG. 11).

TABLE 10

Water consumption by the rats of the various groups (g/kg/d) (mean ± SEM)

| | BC (n = 4) | HSC (n = 4) | PP25 (n = 4) | PP50 (n = 4) | Kruskal-Wallis unpaired analysis |
|---|---|---|---|---|---|
| Week 1 | 92.91 ± 10.02 | 85.91 ± 2.14 | 73.66 ± 3.09 | 79.96 ± 9.10 | H = 4.301 ddl = 3; N.S. |
| Week 2 | 88.10 ± 6.45 | 84.03 ± 2.94 | 74.16 ± 1.20 | 77.03 ± 4.28 | H = 4.985 ddl = 3; N.S. |
| Week 3 | 81.44 ± 7.80 | 79.09 ± 3.57 | 65.70 ± 4.56 | 79.91 ± 10.41 | H = 3.728 ddl = 3; N.S. |

TABLE 10-continued

Water consumption by the rats of the various groups (g/kg/d) (mean ± SEM)

|  | BC (n = 4) | HSC (n = 4) | PP25 (n = 4) | PP50 (n = 4) | Kruskal-Wallis unpaired analysis |
|---|---|---|---|---|---|
| Friedman test | $\chi^2$ = 4.50 ddl = 2 N.S. | $\chi^2$ = 6.50 ddl = 2 p < 0.05 | $\chi^2$ = 4.50 ddl = 2 N.S. | $\chi^2$ = 0.50 ddl = 2 N.S. | — |
| Wilcoxon test Week 1 vs. Week 2 | — | z = 0.365 N.S. | — | — | — |
| Week 2 vs. Week 3 | — | z = 1.826 p < 0.10 | — | — | — |

Interpretation: the rats of the HSC group have a tendency to consume less water after the heat stroke than during the first two weeks of the study.

Antioxidant Activity

On day 17, the factorial measures ANOVA showed a tendency toward heterogeneity between the half-hemolysis times of the rats of the four groups.

The unpaired t test did not show any significant difference between the groups.

The repeated measures ANOVA showed a tendency toward a difference between the half-hemolysis times of the three samples of the rats of the BC group. The paired t test did not show any significant difference between the different samples (table 11).

TABLE 11

Whole-blood half-hemolysis time (min) between the three samples (mean ± SEM)

|  | BC (n = 12) | HSC (n = 11) | PP25 (n = 11) | PP50 (n = 11) | Factorial measures ANOVA |
|---|---|---|---|---|---|
| D0 | 67.28 ± 0.85 | 68.14 ± 1.08 | 70.86 ± 1.56 | 68.48 ± 0.93 | $F_{(3,41)}$ = 1.86 N.S. |
| D15 | 69.84 ± 1.18 | 69.86 ± 1.04 | 70.44 ± 1.41 | 70.05 ± 1.14 | $F_{(3,41)}$ = 0.05 N.S. |
| D17 | 65.23 ± 1.72 | 71.27 ± 2.22 | 69.44 ± 1.01 | 70.49 ± 1.56 | $F_{(3,41)}$ = 2.64 p < 0.10 |
| Repeated measures ANOVA | $F_{(2,22)}$ = 2.71 p < 0.10 | $F_{(2,20)}$ = 1.37 N.S. | $F_{(2,20)}$ = 1.07 N.S. | $F_{(2,20)}$ = 2.03 N.S. |  |

Interpretation: These three samples do not make it possible to demonstrate a modification of the antioxidant activity of the whole blood between the groups of rats. An assay on red blood cells, in addition to the assay on whole blood, would have made it possible to deduce the antioxidant activity of the plasma and to obtain more precise information on the circulating antioxidant activity.

Between samples D0 and D17, the paired t test showed a significant increase in the half-hemolysis time of the rats of the PP50 group (t=2.57, p=0.026) (table 12).

TABLE 12

Whole-blood half-hemolysis time (min) between the samples on D0 and D17 (mean ± SEM)

|  | BC (n = 12) | HSC (n = 11) | PP25 (n = 11) | PP50 (n = 12) | Factorial measures ANOVA |
|---|---|---|---|---|---|
| D0 | 67.28 ± 0.85 | 68.14 ± 1.08 | 70.86 ± 1.56 | 68.26 ± 0.88 | $F_{(3,41)}$ = 1.92 N.S. |
| D17 | 65.23 ± 1.72 | 71.27 ± 2.22 | 69.44 ± 1.01 | 70.75 ± 1.45 | $F_{(3,41)}$ = 2.81 p < 0.10 |
| Paired t test | t = 1.05 N.S. | t = 1.52 N.S. | t = 1.36 N.S. | t = 2.57 N.S. | — |

Interpretation: The treatment at 50 mg/kg of polyphenols makes it possible to increase the whole-blood half-hemolysis time between D0 and D17, this being the result of a more effective antioxidant activity. Under these of treatment (dose, duration) and assay (on whole blood) conditions, only an effect of the polyphenols administered at 50 mg/kg was detected by this method.

Becoming Accustomed to the Aversive Light Stimulus Avoidance Test

Comment: the session for becoming accustomed to the ALSAT was carried out on D15, the day before the heat stroke.

Lever Manipulation Activity

At the end of the 10 minutes of becoming accustomed to the test, the factorial measures ANOVA showed that the total number of times the two levers were pressed by the rats of the various groups were statistically equivalent (table 13; FIG. 12).

TABLE 13

Total number of times the two levers were pressed during the session for growing accustomed to the test (mean ± SEM)

| | BC (n = 16) | HSC (n = 16) | PP25 (n = 16) | PP50 (n = 15) |
|---|---|---|---|---|
| LA + LI | 30.06 ± 4.20 | 23.06 ± 3.14 | 25.81 ± 3.92 | 24.40 ± 3.38 |
| Factorial measures ANOVA | | $F_{(3,59)} = 0.86$ N.S. | | |

Interpretation: before the heat stroke, the rats of the various groups showed the same manipulatory activity.

Discrimination Between the Two Levers

In order to evaluate the discrimination between the active and inactive levers, only the presses during the light phase were taken into account. Only the rats having pressed each lever at least once were taken into account in the statistical analysis.

During the 10 minutes of becoming accustomed to the ALSAT test, the paired t test showed that the rats of the four treatment groups significantly discriminated between the active lever and the inactive lever (table 14; FIG. 13).

TABLE 14

Discrimination between the active and inactive levers during the session for becoming accustomed to the test (mean ± SEM)

| Groups | BC (n = 16) | HSC (n = 16) | PP25 (n = 16) | PP50 (n = 15) |
|---|---|---|---|---|
| LA | 6.63 ± 0.79 | 5.76 ± 0.70 | 6.25 ± 0.57 | 6.20 ± 0.61 |
| LI | 4.63 ± 0.46 | 3.56 ± 0.51 | 3.88 ± 0.55 | 3.73 ± 0.45 |
| Paired t test significance | t = 2.58 $p < 0.05$ | t = 2.48 $p < 0.05$ | t = 3.68 $p < 0.01$ | t = 3.95 $p < 0.01$ |

Interpretation: Before the heat stroke, the rats of all the groups discriminated between the active lever and the inactive lever.

Aversive Light Stimulus Avoidance Test

The ALSAT was carried out on D19, three days after the heat stroke.

Total Number of Times the Two Levers are Pressed

At the end of the 20 minutes of the test, the factorial measures ANOVA showed that the total number of times the two levers were pressed by the rats of the various groups were statistically equivalent (table 15, FIG. 14).

TABLE 15

Total number of times the two levers were pressed during the test (mean ± SEM)

| | BC (n = 16) | HSC (n = 15) | PP25 (n = 15) | PP50 (n = 15) |
|---|---|---|---|---|
| LA + LI | 36.94 ± 7.41 | 30.00 ± 5.39 | 37.47 ± 4.31 | 38.40 ± 6.61 |
| Factorial measures ANOVA | | $F_{(3,57)} = 0.39$ N.S. | | |

Interpretation: after the heat stroke, the rats of the various groups showed the same manipulatory activity.

Discrimination Between the Two Levers

In order to evaluate the discrimination between the active and inactive levers, only the presses during the light phase were taken into account. Only the rats having pressed each lever at least once were taken into account in the statistical analysis.

During the 20 minutes of the test, the paired t test showed that the rats of the BC, PP25 and PP50 groups significantly discriminated between the active lever and the inactive lever, whereas the rats of the HSC group did not show any significant discrimination (table 16; FIG. 15).

TABLE 16

Discrimination between the active and inactive levers during the 20 minutes of the test session (mean ± SEM)

| Groups | BC (n = 15) | HSC (n = 14) | PP25 (n = 14) | PP50 (n = 15) |
|---|---|---|---|---|
| LA | 10.40 ± 1.67 | 7.93 ± 1.23 | 9.71 ± 1.00 | 10.93 ± 1.53 |
| LI | 6.13 ± 0.81 | 6.43 ± 1.00 | 5.64 ± 0.87 | 5.27 ± 0.75 |
| Paired t test significance | t = 3.37 $p < 0.01$ | t = 1.59 N.S. | t = 3.55 $p < 0.01$ | t = 5.82 $p < 0.0001$ |

Interpretation: After the heat stroke, only the rats of the HSC group pressed the two levers in an equivalent manner and therefore no longer showed any discrimination between the two levers. The rats exposed to the heat and treated with the polyphenols continued to discriminate between the active lever and the inactive lever.

Morris Water Maze Test

The Morris water maze test was carried out on D20 and D21, 4 and 5 days after the heat stroke.

In terms of trials 3, 4 and 5, of the mean of trials 3, 4 and 5 and of the retest, the factorial measures ANOVA showed no significant difference within the lag times before reaching the platform zone of the four groups of rats (table 16).

Between the mean of trials 3, 4 and 5 and the retest, the paired t test showed a significant increase in the lag time before reaching the platform zone for the rats of the HSC group. A significant decrease in the lag time before reaching the platform, zone in the rats of the PP50 group and a stability in the rats of the BC and PP25 groups were observed (table 17, FIG. 16).

TABLE 17

| Lag time (s) before reaching the platform zone (mean ± SEM) | | | | |
|---|---|---|---|---|
| | BC (n = 16) | HSC (n = 15) | PP25 (n = 15) | PP50 (n = 15) | Factorial measures ANOVA |
| Trial 3 | 10.56 ± 1.96 | 7.87 ± 1.20 | 7.93 ± 0.85 | 10.33 ± 2.06 | $F_{(3,57)} = 0.84$ N.S. |
| Trial 4 | 6.44 ± 0.71 | 8.47 ± 1.21 | 6.67 ± 1.01 | 9.87 ± 1.75 | $F_{(3,57)} = 1.76$ N.S. |
| Trial 5 | 7.75 ± 1.29 | 6.00 ± 0.44 | 6.27 ± 1.21 | 8.07 ± 1.16 | $F_{(3,57)} = 0.91$ N.S. |
| Repeated measures ANOVA | $F_{(2,30)} = 2.86$ $p < 0.10$ | $F_{(2,28)} = 2.03$ N.S. | $F_{(2,28)} = 0.79$ N.S. | $F_{(2,28)} = 0.48$ N.S. | — |
| Mean of trials 3, 4 and 5 (mean 3, 4, 5) | 8.25 ± 0.98 | 7.44 ± 0.70 | 6.96 ± 0.66 | 9.42 ± 0.95 | $F_{(3,57)} = 1.62$ N.S. |
| Retest | 11.50 ± 2.09 | 15.73 ± 4.02 | 8.53 ± 2.70 | 7.00 ± 1.09 | $F_{(3,57)} = 2.04$ N.S. |
| Paired t test Mean 3, 4, 5 vs retest | t = 1.53 N.S. | t = 2.37 $p < 0.05$ | t = 0.56 N.S. | t = 2.18 $p < 0.05$ | — |

Interpretation: the group exposed to the heat and not treated showed a long-term memory deficit, whereas the groups treated with the polyphenols did not show any memory deficit. The rats of the group treated with 50 mg/kg of polyphenols even improved their performance levels in the retest.

4.4 Conclusions

The results given above show that the administration, in preventive mode, of the polyphenols of brewing co-products, at the doses of 25 and 50 mg/kg/d for 3 weeks, showed protective effects against cognitive disturbances in rats having been subjected to a heat stroke.

Example 5

Examination of the Activity of a Polyphenol-Rich Extract on the Epidermal and Dermal Structures of Human Skin Explants Kept Alive 5.1 Objective The objective of the study presented in this example was to explore the potential activities of various concentrations of polyphenols resulting from the brewing industry, in a formulation or incorporated into culture media, on the epidermal and dermal structures of human skin explants kept alive.

The activities were evaluated by means of a histological assessment of the general morphology of the skin after staining with Masson's trichrome, supplemented (on the batches exhibiting a particular interest) with visualization of the GAGs and with immunolabeling of collagen type III and type IV and laminin-5.

5.2 Materials and Methods

Product Tested

The product to be tested was a polyphenol-rich extract obtained as described in example 2 above. It was tested by topical application, it being incorporated in hydrocerin (a base for magistral preparations) at the concentration of 0.25%, 0.50%, 0.75% and 1.00%. It was also tested while incorporated in the culture medium, in a proportion of 0.025%, 0.050%, 0.075% and 0.100%. Two other products were tested in order to serve as points of comparison: a positive reference containing retinol (Retin-Ox+ Nuit, RoC) and the excipient (hydrocerin).

Ex Vivo Model

During handling, explants were prepared from abdominal plastic surgery residues from a 44-year-old Caucasian woman. The adipose tissue was removed, and then explants approximately 10 mm in diameter were prepared using a circular surgical knife. The explants were then kept alive under conventional cell culture conditions for 10 days.

The explants were divided up into 15 batches of 6 explants and one control batch of 3 explants, according to the distribution below:

TABLE 18

| Batch | | Number of explants |
|---|---|---|
| T0 | Plastic surgery control | 3 explants |
| T | Untreated control | 6 explants |
| R | Positive reference (Retin-Ox+ Nuit) | 6 explants |
| E | Excipient (hydrocerin) | 6 explants |
| P1T | Topical application of 0.25% of PPH-BK | 6 explants |
| P2T | Topical application of 0.50% of PPH-BK | 6 explants |
| P3T | Topical application of 0.75% of PPH-BK | 6 explants |
| P4T | Topical application of 1.00% of PPH-BK | 6 explants |
| P1M | PPH-BK in the medium at 0.025% | 6 explants |
| P2M | PPH-BK in the medium at 0.050% | 6 explants |
| P3M | PPH-BK in the medium at 0.075% | 6 explants |
| P4M | PPH-BK in the medium at 0.1% | 6 explants |
| P1TM | P1T and P1M | 6 explants |
| P2TM | P2T and P2M | 6 explants |
| P3TM | P3T and P3M | 6 explants |
| P4TM | P4T and P4M | 6 explants |

The products to be tested topically were applied to the explants in a proportion of 2 mg per explant (1 mg for the positive reference) on D0, D2, D4, D6 and D8. The products to be tested in the culture medium were incorporated therein at the concentrations indicated. Half the culture medium was renewed on D2, D4, D6 and D8.

At T0, the three explants of the control batch were removed and immediately cut in half. One half was fixed in a standard Bouin's solution, the other half was frozen at −80° C. On D6 and D10, this operation was repeated for three explants of each batch.

After 48 hours of fixing in the standard Bouin's, the samples were dehydrated and paraffin-embedded, then placed in blocks using an embedding station, in order to be able to cut sections. Sections of 5 μm were cut and attached to glass slides for the purpose of carrying out staining procedures.

Sections 7 µm thick were cut from the frozen samples, and then attached to silanized glass slides in order to carry out immunolabeling procedures.

Staining—Immunolabeling

The cell viability and the general morphology were observed on sections stained with Masson's trichrome. This staining consists in immersing the sections in successive baths of stains, so as to specifically stain certain structures (the nuclei in black, the cell cytoplasm in pink, the collagen in green), which makes it possible to facilitate the identification of these structures during the microscopic observation.

The glucosaminoglycans (GAGs) were observed on sections stained with alcian blue-PAS. GAGs are complex polysaccharides found in abundance at the surface of cells, and constitute an important element of extracellular matrices. Neutral GAGs, close to the dermal-epidermal junction (DEJ) are reservoirs of growth factors; acidic GAGs, located in the epidermis and the papillary dermis, are essentially made up of hyaluronic acid, involved in skin hydration. In vivo, GAGs are involved in skin elasticity and hydration. The staining with alcian blue-PAS makes it possible to demonstrate the expression of neutral GAGs along the DEJ, in the form of a purplish-pink band.

The immunolabeling for collagen III and the immunolabeling for collagen IV were carried out on frozen sections. The various types of collagen are major elements of extracellular matrices. Collagen III is a component of the fibrillar dermis and collagen IV is a component of the DEJ. Laminin-5 plays an essential role in the adhesion of keratinocytes to the basal membrane by participating in the formation of anchoring complexes. In vivo, they are involved in the tonicity and mechanical strength of the skin.

The immunolabeling for collagen III was developed with DAB, which shows a brown staining. Counterstaining with Masson's hemalun was carried out on the cell nuclei in order to make them appear blue. The collagen IV and laminin-5 immunolabeling were visualized with FITC, a fluorescent molecule which, when it is excited, emits a green light. Counterstaining with propidium iodide was carried out on the cell nuclei in order to make them appear red.

Microscopic Observations

The microscopic observations were carried out by optical microscopy, using a microscope with the ×40 objective. The photographs were taken with a digital camera and stored using archiving software.

5.3. Results and Discussion

Only the most significant results are presented here.

Microscopic Observation

On D0, the general morphology of the explants is normal. On D6, the morphology of the untreated explants is comparable to that of the explants on D0, which is a good indicator of the survival of the explants (FIG. 17).

On the explants treated with the reference formulation containing retinol, acanthosis (increase in epidermal thickness) is very clear. On the explants treated with the excipient, the epidermal and dermal structures are close to those observed on the untreated explants (FIG. 18).

On the explants treated with the P2T and P2M formulations, the epidermal acanthosis is clear, but less than for the explants treated with the reference containing retinol. For the other explants, the epidermal structure is close to that of the explants treated with the excipient. As regards the collagen network in the papillary dermis, it appears:

to be very dense on the explants on the P1TM batch;
to be dense, in particular along the dermal-epidermal junction, on the explants of the P2TM and P4TM batches;
to be quite dense on the explants of the P4T, P2M, P3M, P4M and P3TM batches;
to be close to that observed on the explants treated with the excipient and on those of the P2T, P3T and P1M batches.

The clearest observations were made after 6 days of survival.

On D10, on the untreated explants, the epidermal structure is normal. The papillary dermis is more or less dense. On the explants treated with the reference formulation containing retinol, epidermal acanthosis is very clear. In the papillary dermis, the collagen forms a more or less dense network along the dermal-epidermal junction. On the explants treated with the excipient, the epidermal and dermal structure is close to that observed on the untreated explants.

On the explants treated with the P4TM formulation, the epidermis is clearly acanthotic, but with the very clear appearance of intolerance. For the other products tested, the epidermal structure is close to that of the explants treated with the excipient. As regards the collagen network in the papillary dermis, it appears:

to be dense in the papillary dermis on the explants of the P2M batch;
to be quite dense on the explants treated with the P2T, P3T, P4T, P3M and P4TM products;
to be more or less dense, close to that observed on the untreated explants, with the P1M, P4M, P1TM, P2TM and P3TM products.

All the parameters evaluated during the microscopic observation of the morphology made it possible to select two batches on which the rest of the evaluation of the activity was carried out. These batches meet several requirements:

innocuousness:
absence of intolerance and of cell alterations;
efficacy:
increase in epidermal thickness;
improved compactness of the collagen network in the papillary dermis;
cost:
low concentration.

Gag Staining

On the untreated explants, the neutral GAGs are quite moderately visualized along the dermal-epidermal junction. They are moderately overexpressed on the explants treated with the positive reference.

The topical application of the PPH-BK product at 0.5%, induces a moderate overexpression. The incorporation of the PPH-BK product at 0.025% in the survival medium induces a clear overexpression (FIG. 19).

These results indicate that the PPH-BK product, applied topically, at the concentration of 0.5%, induces an improvement in one of the parameters associated with hydration of the skin, comparable to that induced by the positive reference. When it is incorporated into the medium at the concentration of 0.025%, this improvement is much greater.

Laminin-5 Immunolabeling

On the untreated explants, laminin-5 is clearly visualized forming a thin strip festooned along the dermal-epidermal junction. It is slightly overexpressed on the explants treated with the positive reference.

The topical application of the PPH-BK product at 0.5% induces a moderate overexpression along the dermal-epidermal junction and a clear expression in the basal keratinocytes. The incorporation of the PPH-BK product at 0.025% in the survival medium induces a slight overexpression at the level of the dermal-epidermal junction and the basal keratinocytes (FIG. 20).

These results indicate that the PPH-BK product, applied topically at the concentration of 0.5%, induces an increase in expression which is much greater than that induced by the positive reference. When it is incorporated into the medium at the concentration of 0.025%, the increase in expression is slightly greater than that obtained with the reference.

Collagen III Immunolabeling

On the untreated explants, collagen III is slightly visualized forming a not very dense network in the papillary dermis, along the dermal-epidermal junction. It is moderately overexpressed on the explants treated with the positive reference.

The topical application of the PPH-BK product at 0.5% induces a clear overexpression. The incorporation of the PPH-BK product at 0.025% in the survival medium induces a slight overexpression (FIG. 21).

These results indicate that the PPH-BK product, applied topically at the concentration of 0.5%, induces an increase in expression which is greater than that induced by the positive reference. When it is incorporated into the medium at the concentration of 0.025%, the increase in expression is comparable to that obtained with the reference.

Collagen IV Immunolabeling

On the untreated explants, collagen IV is clearly visualized along the dermal-epidermal junction. It is relatively irregular and moderately present in the underlying papillary dermis. It is clearly overexpressed on the explants treated with the positive reference.

The topical application of the PPH-BK product at 0.5% induces a clear overexpression, especially along the dermal-epidermal junction. The incorporation of the PPH-BK product at 0.025% in the survival medium induces a clear overexpression, especially along the dermal-epidermal junction (FIG. 22).

These results indicate that the PPH-BK product, applied topically at the concentration of 0.5%, or incorporated into the medium at the concentration 0.025%, induces an increase in expression comparable to that induced by the positive reference.

5.4 Conclusion

The results are summarized in the table below.

TABLE 19

| Batch | Number of epidermal cell strata | | Epidermal morphology | | Collagen density | |
|---|---|---|---|---|---|---|
| | D6 | D10 | D6 | D10 | D6 | D10 |
| T | 4/5 | 5/6 | OK | OK | +/− dense | +/− dense |
| R | 13/14 | 13/14 | Odema | Strong odema | +/− dense | +/− dense |
| E | 5/6 | 4/5 | OK | OK | +/− dense | Not very dense |
| P2T | 7/8 | 3/4 | OK | OK | +/− dense | Quite dense |
| P3T | 5/6 | 4/5 | OK | OK | +/− dense | Quite dense |
| P4T | 7/8 | 4/5 | OK | OK | Quite dense | Quite dense |
| P1M | 5/6 | 5/6 | OK | OK | +/− dense | +/− dense |
| P2M | 4/5 | 4/5 | OK | OK | Quite dense | Dense |
| P3M | 5/6 | 4/5 | OK | OK | Quite dense | Quite dense |
| P4M | 4/5 | 4/5 | OK | OK | Quite dense | +/ |
| P1TM | 5/5 | 4/5 | OK | OK | Very dense | +/ |

TABLE 19-continued

| Batch | Number of epidermal cell strata | | Epidermal morphology | | Collagen density | |
|---|---|---|---|---|---|---|
| | D6 | D10 | D6 | D10 | D6 | D10 |
| P2TM | 5/6 | 4/5 | OK | OK | Dense | +/ |
| P3TM | 5/6 | 4/5 | Quite good | Quite good | Quite dense | +/ |
| P4TM | 5/6 | 7/8 | Altered | Very altered | Quite dense | Quite dense |

These results show that, using the two methods of application tested (topical application or incorporation in the medium), the product induces an increase in the expression of several parameters associated with hydration, elasticity and youthfulness of the skin, from 6 days onward. Moreover, its effect on these parameters is comparable to or greater than that of a reference cream containing retinol.

This indicates that the polyphenols extracted from the brewing process can be of use in the cosmetics industry at least in the following applications:
antioxidant
anti-aging (increase in epidermal thickness)
moisturization.

Example 6

Composition of the Polyphenol Extracts Obtained 6.1 Evaporation of the Samples

Aim of the Tests

To observe the behavior of be products undergoing evaporation and to determine their boiling retardation.

To determine the exchange coefficients at the various steps of concentration.

To observe their ability to be concentrated and to predict the quality of the condensates.

Procedure

The tests were carried out, batchwise, on an industrial evaporator of falling film type under a slightly reduced pressure (P=0.25 bar abs, Teq=65° C.)

The tests were carried out in three distinct batches: A, B, C. Each batch representing a volume of V=100 l.

Characteristics of the Effluent

Crude product dry matter 1.5%

Description black with strong odor of alcohol.

Behavior During Evaporation

Batch A:

Start of the concentration: cubitainer volume=100 l

End of the concentration: volume in the evaporator=15 l

The concentration factor by volume obtained is therefore 6.6.

Residence time in the evaporator: 2 h.

At the end of the test, a deposit on the top of the walls of the evaporator is observed.

However, said evaporator can be cleaned very well with a solution of alcohol.

Batch B:

Start of the concentration: cubitainer volume=95 l.

End of the concentration: volume in the evaporator=25 l.

The concentration factor by volume obtained is therefore 3.8.

Residence time in the evaporator: 1 h 40.

At the end of the test, it is noted that there is no deposit on the top of the walls of the evaporator. The concentrate still has an odor of alcohol.

Batch C:

Start of the concentration: cubitainer volume=100 l.

End of the concentration: volume in the evaporator=30 l.

The concentration factor by volume obtained is therefore 3.3.

Residence time in the evaporator: 1 h 45.

At the end of the test, it is noted that there is no deposit on the top of the walls of the evaporator. The concentrate still has an odor of alcohol.

6.2 Sample Analysis

The samples obtained by evaporation were subsequently freeze-dried and analyzed by high performance liquid chromatography (HPLC). The results are given in the tables below and also in FIG. 23.

TABLE 20

Analysis of the freeze-dried samples

| | | Powder A | Powder B | Powder C |
|---|---|---|---|---|
| mg/g | Iron | 0 | 0 | 0 |
| | Copper | 0.003 | 0.003 | 0.0005 |
| | Calcium | 2.848 | 1.094 | 1.227 |
| | Magnesium | 0.428 | 0.231 | 0.263 |
| | Potassium | 0.436 | 0 | 0 |
| | Sodium | 3.469 | 0.585 | 0.687 |
| | Zinc | 0.011 | 0.009 | 0.007 |
| | Chlorides (Cl) | 5.73 | 0.609 | 0.4 |
| | Sulfates | 1.555 | 0.557 | 0.801 |
| | Nitrates | 0 | 0 | 0 |
| | Free oxalic acid | 1.687 | 0 | 0.233 |
| | Lead | 0 | 0 | 0 |
| | Cadmium | 0 | 0 | 0 |
| | Chromium | 0 | 0 | 0 |
| | Arsenic | 0 | 0 | 0 |
| | Aluminum | 0.002 | 0.002 | 0.002 |
| | Titanium nitride | 0 | 0 | 0 |
| | Cobalt | 0 | 0 | 0 |
| | Mercury | 0 | 0 | 0 |
| | Manganese | 0 | 0 | 0 |
| | Phosphorus | 1.73 | 1.66 | 1.8 |
| | Nickel | 0 | 0 | 0 |
| | Total minerals mg/g | 17.899 | 4.75 | 5.4205 |
| | Total minerals % | 1.7899 | 0.475 | 0.54205 |
| | Total sugars mg/g | 0.47 | 0.33 | 0.33 |
| | Total sugars % | 0.047 | 0.033 | 0.033 |
| | % Total proteins/WM | 1.1 | 1.8 | 1.8 |
| | Moisture content % | 1 | 2.1 | 1.8 |
| | Polyphenols mg/g EBC method | 697 | 735 | 865 |
| | % Polyphenols EBC | 69.7 | 73.5 | 86.5 |
| | Polyphenols mg/g Gallic acid equ. | 320 | 338 | 399 |
| | Polyphenols Folin-Ciocalteu mg/g gallic acid equ. | 478 | 529 | 483 |
| | % | 47.8 | 52.9 | 48.3 |
| | DDPH antioxidant powder mg/g of polyphenols (EBC) | 3796 | 3523 | 3244 |
| After hydrolysis | Fructose (W/V) | 0 | 0 | 0 |
| | Glucose (W/V) | 0 | 0 | 0 |
| | Sucrose (W/V) | 0 | 0 | 0 |
| | Maltose (W/V) | 0 | 0 | 0 |
| | Maltotriose (W/V) | 0 | 0 | 0 |

TABLE 21

Flavanol and phenolic acid compositions (% by mass)

| | A | B | C |
|---|---|---|---|
| Catechin | 38.75 | 30.77 | 27.68 |
| Epicatechin | 34.62 | 22.70 | 24.83 |
| Tyrosol | 11.79 | 11.13 | 8.86 |
| Ferulic acid | 14.30 | 12.74 | 13.10 |
| Total % flavanols + ferulic acid | 99.46 | 77.34 | 74.46 |

TABLE 22

Mass balance

| | A | B | C |
|---|---|---|---|
| Total flavanols and phenolic acids | 99.46 | 77.34 | 74.46 |
| Total proteins | 1.10 | 1.80 | 1.80 |
| Minerals | 1.79 | 0.48 | 0.54 |
| Sugars | 0.05 | 0.03 | 0.03 |
| Moisture content | 1.00 | 2.10 | 1.80 |
| Total | 103.40 | 81.75 | 78.64 |

REFERENCES

Blokland A, Geraerts E, Been M. A detailed analysis of rats' spatial memory in a probe trial of a Morris task. *Behavioral Brain Research*. 2004, 154(1): 71-5.

Brand-Williams W., Cuvelier M. E. and Berset C., Use of a Free Radical Method to Evaluate Antioxidant Activity. *Lebensm. Wiss. Technol.*, 1995, 28(1), 25-30.

Brouillard R., George F. and Fougerousse A., Polyphenols produced during red wine ageing. *BioFactors*, 1997, 6(4), 403-410.

Canini F, Buguet A, Bourdon L. Inhibition of different types of nitric oxide synthase: effect on thermoregulation in the rat exposed to high ambient temperature. *Neurosciences Letters*, 2001, 316(1): 45-9.

Folin O. and Ciocalteu V., On Tyrosine and Tryptophane Determinations in Proteins. *J. Biol. Chem.*, 1927, 73(2), 627-650.

McMurrough I., Roche G. P. and Cleary K. G., Phenolic acids in beers and worts. *J. Inst. Brew.*, 1984, 90(3), 181-187.

Messaoudi M, Tricoire A, Lalonde R, Canini F, Minn A. Effects of MPTP on lever-pressing for light extinction in rats. *European Journal of Pharmacology*, 1996, 299: 17-20.

Messaoudi M, Desor D, Grasmück V, Joyeux M, Langlois A, Roman F J. Behavioral evaluation of visceral pain in a rat model of colonic inflammation. *Neuroreport*, 1999, 10: 1137-1141.

Morris R G, Garrud P, Rawlins J N, O'Keefe J. Place navigation impaired in rats with hippocampal lesions. *Nature*, 1982, 297(5868): 681-3.

Prost, M. Process for the determination by means of free radicals on the antioxidant properties of a living organism or potentially aggressive agents. 1992, U.S. Pat. No. 5,135, 850.

Tubaro F., Rapuzz i P. and Ursini A. F., Kinetic analysis of antioxidant capacity of wine *BioFactors*, 1999, 9(1), 37-47.

Yang C Y, Lin M T. Oxidative stress in rats with heatstroke-induced cerebral ischemic. *Stroke,* 2002, 33: 790-794.

The invention claimed is:

1. A method of treating dry and/or aging skin comprising topically administering to a subject in need thereof a cosmetic product comprising an effective amount of a polyphenol concentrate,
   wherein the polyphenol concentrate comprises catechin, epicatechin, tyrosol and ferulic acid, and
   wherein the polyphenol concentrate is obtained from partially purified beer by a process comprising the steps of:
   (a) contacting partially purified beer containing polyphenols with a polyvinylpolypyrrolidone (PVPP) resin to adsorb the polyphenols to the resin,
   (b) washing the PVPP resin and adsorbed polyphenols with an alkaline solution to produce a PVPP washing solution,
   (c) contacting the PVPP washing solution with a second resin to adsorb the polyphenols to the second resin, the second resin being hydrophobic and nonionic,
   (d) passing an organic solvent over the second resin to desorb the polyphenols from the resin, and
   (e) collecting and concentrating the polyphenols to produce the polyphenol concentrate.

2. The method as claimed in claim 1, wherein in step (b) the PVPP undergoes two washes with sodium hydroxide solution, whereby only the sodium hydroxide solution from the first wash is used in step (c).

3. The method as claimed in claim 1, in which the alkaline solution used for washing the PVPP is neutralized or acidified before carrying out step (c).

4. The method as claimed in claim 1, in which the second resin is rinsed with an aqueous solution between steps (c) and (d).

* * * * *